(12) United States Patent
Koseoglu

(10) Patent No.: US 12,354,712 B2
(45) Date of Patent: Jul. 8, 2025

(54) METHOD TO PREPARE VIRTUAL ASSAY USING NUCLEAR MAGNETIC RESONANCE SPECTROSCOPY

(71) Applicant: Saudi Arabian Oil Company, Dhahran (SA)

(72) Inventor: Omer Refa Koseoglu, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 620 days.

(21) Appl. No.: 17/681,894

(22) Filed: Feb. 28, 2022

(65) Prior Publication Data

US 2023/0274804 A1 Aug. 31, 2023

(51) Int. Cl.
| G16C 20/30 | (2019.01) |
| G01N 24/08 | (2006.01) |
| G01N 33/28 | (2006.01) |
| G16C 20/20 | (2019.01) |

(52) U.S. Cl.
CPC ........... *G16C 20/30* (2019.02); *G01N 24/081* (2013.01); *G01N 33/2835* (2013.01); *G01N 33/287* (2013.01); *G16C 20/20* (2019.02)

(58) Field of Classification Search
None
See application file for complete search history.

(56) References Cited

U.S. PATENT DOCUMENTS

| 3,617,501 A | 11/1971 | Eng |
| 3,896,312 A | 7/1975 | Brown |
| 4,251,870 A | 2/1981 | Jaffe |
| 4,897,177 A | 1/1990 | Nadler |
| 4,971,915 A | 11/1990 | Schwartz et al. |
| 4,988,446 A | 1/1991 | Haberman |
| 5,121,337 A | 6/1992 | Brown |
| 5,223,714 A | 6/1993 | Maggard |
| 5,266,800 A | 11/1993 | Mullins |
| 5,304,807 A | 4/1994 | Lin |
| 5,424,959 A | 6/1995 | Reyes |
| 5,452,232 A | 9/1995 | Espinosa et al. |

(Continued)

FOREIGN PATENT DOCUMENTS

| CA | 2781273 A1 | 12/2013 |
| EP | 0305090 A2 | 8/1988 |

(Continued)

OTHER PUBLICATIONS

ES2543338T3 translation (Year: 2015).*

(Continued)

*Primary Examiner* — Lina Cordero
(74) *Attorney, Agent, or Firm* — Leason Ellis LLP

(57) ABSTRACT

Systems and methods are disclosed for providing virtual assays of an oil sample such as crude oil based on nuclear magnetic resonance (NMR) spectroscopy carried out on the oil sample, and the density of the oil sample. The virtual assay provides a full range of information about fractions of the oil sample including naphtha, gas oil, vacuum gas oil, vacuum residue, and other information about the properties of the oil sample. Using the system and method herein, the virtual assay data pertaining to these several fractions of the oil sample and the oil sample itself are obtained without fractionation of the oil sample into the several components.

18 Claims, 5 Drawing Sheets

(56) References Cited

U.S. PATENT DOCUMENTS

| | | | |
|---|---|---|---|
| 5,475,612 A | 12/1995 | Espinosa | |
| 5,490,085 A | 2/1996 | Lambert et al. | |
| 5,572,030 A | 11/1996 | Ranson et al. | |
| 5,600,134 A | 2/1997 | Ashe et al. | |
| 5,602,755 A | 2/1997 | Ashe et al. | |
| 5,656,810 A | 8/1997 | Alfano et al. | |
| 5,699,269 A | 12/1997 | Ashe et al. | |
| 5,699,270 A | 12/1997 | Ashe et al. | |
| 6,070,128 A | 5/2000 | Descales | |
| 6,258,987 B1 | 7/2001 | Schmidt et al. | |
| 6,275,775 B1 | 8/2001 | Baco | |
| 6,490,029 B1 | 12/2002 | Cho | |
| 6,602,403 B1 | 8/2003 | Steffens et al. | |
| 6,611,735 B1 | 8/2003 | Henly | |
| 6,633,043 B2 | 10/2003 | Hegazi | |
| 6,662,116 B2 | 12/2003 | Brown | |
| 6,711,532 B1 | 3/2004 | Spieksma | |
| 6,841,779 B1 | 1/2005 | Roehner et al. | |
| 6,893,874 B2 | 5/2005 | Stark | |
| 7,126,332 B2 | 10/2006 | Blanz | |
| 7,173,239 B2 | 2/2007 | DiFoggio | |
| 7,560,711 B2 | 7/2009 | Hegazi | |
| 7,598,487 B2 | 10/2009 | Qian | |
| 8,714,246 B2 | 5/2014 | Pop et al. | |
| 8,930,149 B1 | 1/2015 | Koseoglu et al. | |
| 9,285,307 B2 | 3/2016 | Koseoglu et al. | |
| 9,423,391 B2 | 8/2016 | Koseoglu et al. | |
| 9,429,556 B2 | 8/2016 | Koseoglu et al. | |
| 9,778,240 B2 | 10/2017 | Koseoglu et al. | |
| 9,816,919 B2 | 11/2017 | Koseoglu et al. | |
| 10,684,239 B2 | 6/2020 | Koseoglu et al. | |
| 10,899,983 B1 * | 1/2021 | Kar | C10L 1/04 |
| 2002/0052769 A1 | 5/2002 | Navani et al. | |
| 2003/0141459 A1 | 7/2003 | Hegazi et al. | |
| 2003/0195708 A1 | 10/2003 | Brown | |
| 2005/0109934 A1 | 5/2005 | David | |
| 2005/0173298 A1 | 8/2005 | Wellington | |
| 2006/0043004 A1 | 3/2006 | Rose | |
| 2006/0047444 A1 | 3/2006 | Brown | |
| 2006/0142955 A1 | 6/2006 | Jones | |
| 2007/0050154 A1 | 3/2007 | Albahri | |
| 2007/0231912 A1 | 10/2007 | Reischman et al. | |
| 2007/0295640 A1 | 12/2007 | Tan et al. | |
| 2008/0037006 A1 | 2/2008 | Canas Triana | |
| 2008/0040051 A1 | 2/2008 | Franklin et al. | |
| 2008/0206887 A1 | 8/2008 | Chen | |
| 2008/0248967 A1 | 10/2008 | Butler et al. | |
| 2008/0253426 A1 | 10/2008 | Voelkening | |
| 2008/0260584 A1 | 10/2008 | Gudde et al. | |
| 2009/0011517 A1 | 1/2009 | Hodges | |
| 2009/0180949 A1 | 7/2009 | Cui | |
| 2009/0279072 A1 | 11/2009 | Arakawa | |
| 2009/0290144 A1 | 11/2009 | Hegazi | |
| 2009/0316139 A1 | 12/2009 | Shrestha | |
| 2010/0049681 A1 | 2/2010 | Pradhan | |
| 2010/0113311 A1 | 5/2010 | Eccleston et al. | |
| 2010/0204925 A1 | 8/2010 | Albahri | |
| 2010/0211329 A1 | 8/2010 | Farquharson et al. | |
| 2010/0218585 A1 | 9/2010 | Chawla | |
| 2011/0152136 A1 | 6/2011 | Hughes et al. | |
| 2011/0308996 A1 | 12/2011 | Choudhary | |
| 2012/0171151 A1 | 7/2012 | Thomassian | |
| 2014/0075827 A1 | 3/2014 | Gonzalez et al. | |
| 2014/0156241 A1 | 6/2014 | Kumar et al. | |
| 2015/0106027 A1 | 4/2015 | Koseoglu et al. | |
| 2015/0106028 A1 | 4/2015 | Koseoglu et al. | |
| 2015/0106029 A1 | 4/2015 | Koseoglu et al. | |
| 2015/0106031 A1 | 4/2015 | Koseoglu et al. | |
| 2015/0112610 A1 | 4/2015 | Koseoglu | |
| 2015/0112611 A1 | 4/2015 | Koseoglu | |
| 2016/0011102 A1 | 1/2016 | Koseoglu et al. | |
| 2016/0187253 A1 | 6/2016 | Koseoglu et al. | |
| 2016/0195481 A1 | 7/2016 | Koseoglu | |
| 2016/0195507 A1 | 7/2016 | Koseoglu | |
| 2016/0195508 A1 | 7/2016 | Al-Hajji | |
| 2016/0377589 A1 | 12/2016 | Koseoglu | |
| 2017/0003217 A1 | 1/2017 | Koseoglu | |
| 2017/0363540 A1 | 12/2017 | Koseoglu | |
| 2017/0363591 A1 | 12/2017 | Koseoglu | |
| 2017/0363602 A1 | 12/2017 | Koseoglu | |
| 2017/0363603 A1 | 12/2017 | Koseoglu | |
| 2018/0011037 A1 * | 1/2018 | Koseoglu | G01R 33/4625 |

FOREIGN PATENT DOCUMENTS

| | | | |
|---|---|---|---|
| EP | 0304232 A2 | 2/1989 | |
| EP | 0552300 A1 | 7/1993 | |
| EP | 0794433 A1 | 9/1997 | |
| EP | 0859236 A1 | 8/1998 | |
| EP | 0984277 A1 | 3/2000 | |
| ES | 2543338 T3 * | 8/2015 | C10G 49/26 |
| SU | 817486 A1 | 3/1981 | |
| SU | 1523972 A1 | 11/1989 | |
| WO | 03/048759 A1 | 6/2003 | |
| WO | 2004033513 A2 | 4/2004 | |
| WO | 2006030218 A1 | 3/2006 | |
| WO | 2009082418 A2 | 7/2009 | |
| WO | 2013102916 A1 | 7/2013 | |

OTHER PUBLICATIONS

Adhvaryu, A. et al., Quantitative NMR Spectroscopy for the Prediction of Base Oil Properties, Tribology Transactions, vol. 43, No. 2, 2000, pp. 245-250.

Albahri, T. et al., Octane Number and Aniline Point of Petroleum Fuels, 2002, Fuel Chemistry Division, vol. 47(2), pp. 710-711.

Ali, M., Resolution and Quantification of Ring Type Aromatics by HPLC Method using N-Hexane Elution, 2003, King Fahd University of Petroleum and Minerals, pp. 1-9.

ASTM D2887-01, Standard Test Method for Boiling Range Distribution of Petroleum Fractions by Gas Chromatography, Annual Book of ASTM Standards, vol. 14, No. 02, pp. 204-216.

Birch C., Oil & Gas Journal, Jan. 14, 2002, pp. 54-59 (printed Jul. 9, 2014 from http://www.ogj.com/articles/print/volume-100/issue-2/processing/achieving-maximum-crude-oil-value-depends-on-accurate-evaluation.html).

Bowden, J. et al., Octane-Cetane Relationship, 1974, NTIS, p. 8.

Chemstations, Inc., Physical Properties User's Guide, 2004, Chemstations Inc., Ver. 5.4, pp. 18-22.

Cookson, D.J. et al., Investigation of the Chemical Basis of Diesel Fuel Properties, Energy & Fuels, vol. 2, No. 6, 1988, pp. 854-860.

Duvekot, C., Fast Analysis of Paraffins, iso-Paraffins, Olefins, iso-Olefins, Naphthenes and Aromatics in Hydrocarbon Streams, Varian, Inc., 2008, pp. 1-4.

Evokimov, I, et al, Potential of UV-Visible Absorption Spectroscopy for characterizing Crude Petroleum Oils, Oil an Gas Business, 2007, 21 pages.

Falla, F, et al., Characterization of crude petroleum by NIR, Journal of Petroleum Science and Engineering, vol. 51, 2006, pp. 127-137.

Fernandez-Lima, F. et al., Petroleum Crude Oil Characterization by IMS-MS and FTICR MS, 2009, American Chemical Society, Ed. 81, pp. 9941-9945.

Grizzle, P. et al., Automated Liquid Chromatographic Compound Class Group-Type Separation of Crude Oils and Bitumens Using Chemically Bonded Aminolilane, 1986, Publisher Anal. Chem., vol. 58, pp. 2389-2390.

Hasan, M.U. et al., Structural characterization of Saudi Arabian heavy crude oil by n.m.r. spectroscopy, Fuel, vol. 62, 1983, pp. 518-523.

Hidajat, K, et al., Quality characterisation of crude oils by partial least square calibration of NIR spectral profiles, Near Infrared Spectrosc, vol. 8, pp. 53-59, 2000.

Jokuty, P. et al., Hydrocarbon Groups and Their Relationships to Oil Properties and Behavior, 1995, Published by Whiticar Scientific, p. 11.

Khanmohammadi, M, et al., Characterization of petroleum-based products by infrared spectroscopyu and chemometrics, Trac Trends in Analytical Chem, vol. 35, 2012.

(56) References Cited

OTHER PUBLICATIONS

Kok, M, et al., High pressure TGA analysis of crude oils, Thermochimica Acta., vol. 287, No. 1, 1996, pp. 91-99.

Mckenna, Amy M., Heavy Petroleum Composition. 1. Exhaustive Compositional Analysis of Athabasca Bitumen HVGO Distillates by Fourier Transform Ion Cyclotron Resonance Mass Spectrometry: A Definitive Test of the Boduszynski Model, Energy Fuels, 24, 2010, pp. 2929-2038.

Mohammed, S., The Use of Compounds Chemically Related to Analyte as Surrogate Reference Standards in Quantitative HPLC, Feb. 2008, Produced by Kwame Nkrumah University of Science and Technology, Kumasi, p. 16.

Pande, S., et al., Cetana No. Predictions of a Trial Index Based on Compositional Analysis, American Chemical Society, 1989, pp. 308-312.

Patra, D, et al., Determination of Synchronous Fluorescence Scan Parameters for Certain Petroleum Products, Journal of Scientific & Industrial Research, Apr. 1, 2000, pp. 300-305.

Pavlovic K., Oil & Gas Journal, Nov. 22, 1999, pp. 51-56 (printed Jul. 9, 2014 from http://www.ogj.com/articles/print/volume-97/issue-47/in-this-issue/refining/gravity-and-sulfur-based-crude-valuations-more-accurate-than-believed.html).

Pereira, Thieres M. C., An evaluation of the aromaticity of asphaltenes using atmospheric pressure photoionization Fourier transform ion cyclotron resonance mass spectrometry—APP (±) FT-ICR MS, Fuel, 2014, vol. 118, 2014, pp. 348-357.

Rodgers, R. et al., Advanced Characterization of Petroleum Crude and Products by High Field Fourier Transform Ion Cyclotron Resonance Mass Spectrometry, 2002, Fuel Chemistry Division, Ed. 47(2), pp. 636-637.

Shea, T.M., Modeling Base Oil Properties using NMR Spectroscopy and Neural Networks, Tribology Transactions, vol. 46, No. 3, 2003, pp. 296-302.

Souza, C. et al., Cetane Number Assessment in Diesel Fuel by 1H or Hydrogen Nuclear Magnetic Resonance-Based Multivariate Calibration, Energy & Fuels, vol. 28, 2014, pp. 4958-4962.

Speight, Handbook of Petroleum Product Analysis, 2002.

Terra, L. et al., Petroleomics by electrospray ionization FT-ICR mass spectrometry coupled to partial least squares with variable selection methods: prediction of the total acid number of crude oils, 2014, Analyst, vol. 139, 2014, pp. 4908-4916.

University of Oldenburg, Institute of Physics, Catalogue of Optical Spectra of Oils, Jan. 2005, retrieved from http://las.physik.uni-oldenburg.de/data/spectra/index.htm, 6 pages.

Yamashita, G.T., Evaluation of Integration Procedures for PNA Analysis by C-13 NMR, Symposium on Analytical Chemistry of Heavy Oils/Resids Presented Before the Division of Petroleum Chemistry, Inc., American Chemical Society, Dallas Meeting, Apr. 9-14, 1989, pp. 301-305.

PCT/US2016/012115, International Search Report and Written Opinion dated May 12, 2016, 16 pages.

Office Action in corresponding SA Application No. 123441304, mailed May 29, 2024; 15 pages.

* cited by examiner

METHOD TO PREPARE VIRTUAL ASSAY USING NUCLEAR MAGNETIC RESONANCE SPECTROSCOPY

RELATED APPLICATIONS

Not applicable.

BACKGROUND

Field of the Invention

The present invention relates to methods and systems for evaluating an oil sample such as crude oil to provide a virtual assay.

Description of Related Art

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. In addition to crude oils varying from one geographical region to another and from field to field, it has also been observed that the properties of the crude oil from one field may change with time, as oil is withdrawn from different levels or areas of the field. Depending on the source and/or time of withdrawal, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and other elements in quantities that impact the refinery processing of the crude oil fractions. Light crude oils or condensates can contain sulfur in concentrations as low as 0.01 W %; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

A crude oil assay is a traditional method of determining the nature of crude oils for benchmarking purposes. Crude oils are subjected to true boiling point (TBP) distillations and fractionations to provide different boiling point fractions. The crude oil distillations are carried out using the American Standard Testing Association (ASTM) Method D 2892. Common fractions and their corresponding nominal boiling points or boiling point ranges are given in Table 1.

The yields, composition, physical and indicative properties of these crude oil fractions, where applicable, are then determined during the crude assay work-up calculations. Typical compositional and property information obtained from a crude oil assay is given in Table 2.

Due to the number of distillation cuts and the number of analyses involved, the crude oil assay work-up is both costly and time consuming. In a typical refinery, crude oil is first fractionated in the atmospheric distillation column to separate sour gas and light hydrocarbons, including methane, ethane, propane, butanes and hydrogen sulfide, naphtha (for instance having a nominal boiling point range of about 36-180° C.), kerosene (for instance having a nominal boiling point range of about 180-240° C.), gas oil (for instance having a nominal boiling point range of about 240-370° C.) and atmospheric residue (for instance having a nominal boiling point range of about >370° C.). The atmospheric residue from the atmospheric distillation column is either used as fuel oil or sent to a vacuum distillation unit, depending on the configuration of the refinery. The principal products obtained from vacuum distillation are vacuum gas oil (for instance having a nominal boiling point range of about 370-520° C.) and vacuum residue (for instance having a nominal boiling point range of about >520° C.). Crude assay data is conventionally obtained from individual analysis of these cuts, separately for each type of data sought for the assay (that is, elemental composition, physical property and indicative property), to help refiners to understand the general composition of the crude oil fractions and properties so that the fractions can be processed most efficiently and effectively in an appropriate refining unit. Indicative properties are used to determine the engine/fuel performance or usability or flow characteristic or composition.

Whole Crude Oil Properties Many properties are routinely measured for crudes. Some of the most common factors affecting crude oil handling, processing, and value include the following: density; viscosity; pour point; Reid vapor pressure (RVP); carbon residue; sulfur; nitrogen; metals; salt content; hydrogen sulfide; Total Acidity Number (TAN). These are described in more detail below:

Density, measured for example by the ASTM D287 method, is the weight of a substance for a given unit of volume. Density of crude oil or crude products is measured as specific gravity comparing the density of the crude or product to the density of water (usually expressed as gm/cc) or API gravity (° API or degrees API).

Viscosity, measured for example by the ASTM D 445 method, is the measure of the resistance of a liquid to flow, thereby indicating the pumpability of the oil. Kinematic viscosity is the viscosity of the material divided by the density (specific gravity) of the material at the temperature of viscosity measurement; kinematic viscosity is commonly measured in stokes (St) or centistokes (cSt).

Pour point, measured for example by the ASTM D97 method, is the temperature, to the next 5° F. increment, above which an oil or distillate fuel becomes solid. The pour point is also the lowest temperature, in 5° F. increments, at which the fluid will flow. After preliminary heating, the sample is cooled at a specified rate and examined at intervals of 3° C. for flow characteristics. The lowest temperature at which movement of the specimen is observed is recorded as the pour point.

Reid vapor pressure (RVP), measured for example by the ASTM D323 method, is the measure of the vapor pressure exerted by an oil, mixed with a standard volume ratio of air, at 100° F. (38° C.).

Carbon residue, measured for example by the ASTM D189, D4536 methods, is the percentage of carbon by weight for coke, asphalt, and heavy fuels found by evaporating oil to dryness under standard laboratory conditions. Carbon residue is generally termed Conradson Carbon Residue, or CCR.

Sulfur is the percentage by weight, or in parts per million by weight, of total sulfur contained in a liquid hydrocarbon sample. Sulfur must be removed from refined product to prevent corrosion, protect catalysts, and prevent environmental pollution. Sulfur is measured, for example, by ASTM D4294, D2622, D5453 methods for gasoline and diesel range hydrocarbons.

Nitrogen, measured for example by the ASTM D4629, D5762 methods, is the weight in parts per million, of total nitrogen contained in a liquid hydrocarbon sample. Nitrogen compounds are also catalyst poisons.

Various metals (arsenic, lead, nickel, vanadium, etc.) in a liquid hydrocarbon are potential process catalyst poisons. They are measured by Induced Coupled Plasma and/or Atomic Absorption Spectroscopic methods, in ppm.

Salt is measured, for example, by the ASTM D3230 method and is expressed as pounds of salt (NaCl) per 1000 barrels of crude. Salts are removed prior to crude oil distillation to prevent corrosion and catalyst poisoning.

Hydrogen sulfide ($H_2S$) is a toxic gas that can be evolved from crude or products in storage or in the processing of crude. Hydrogen sulfide dissolved in a crude stream or product stream is measured in ppm.

Total acidity is measured, for example, by the ASTM methods, D664, D974, and is a measure of the acidity or alkalinity of an oil. The number is the mass in milligrams of the amount of acid (HCl) or base (KOH) required to neutralize one gram of oil.

These properties affect the transportation and storage requirements for crudes, define the products that can be extracted under various processing schemes, and alert us to safety and environmental concerns. Each property can also affect the price that the refiner is willing to pay for the crude. In general, light, low sulfur crudes are worth more than heavy, high sulfur crudes because of the increased volume of premium products (gasoline, jet fuel, and diesel) that are available with minimum processing.

Crude Assays

A crude assay is a set of data that defines crude composition and properties, yields, and the composition and properties of fractions. Crude assays are the systematic compilation of data defining composition and properties of the whole crude along with yields and composition and properties of various boiling fractions. For example, a conventional assay method requires approximately 20 liters of crude oil be transported to a laboratory, which itself can be time-consuming and expensive, and then distilled to obtain the fractions and then have analysis performed on the fractions. This systematic compilation of data provides a common basis for the comparison of crudes. The consistent presentation of data allows us to make informed decisions as to storage and transportation needs, processing requirements, product expectations, crude relative values, and safety and environmental concerns. It also allows us to monitor crude quality from a single individual source over a period of time.

Crude oils or fractions are evaluated and compared using some of the key properties that are indicative of their performance in engines. These are the cetane number, the cloud point, the pour point (discussed above), the aniline point, and the flash point. In instances where the crude is suitable for production of gasoline, the octane number is another key property. These are described individually herein.

The cetane number of diesel fuel oil, determined by the ASTM D613 method, provides a measure of the ignition quality of diesel fuel; as determined in a standard single cylinder test engine; which measures ignition delay compared to primary reference fuels. The higher the cetane number; the easier the high-speed; direct-injection engine will start; and the less white smoking and diesel knock after start-up are. The cetane number of a diesel fuel oil is determined by comparing its combustion characteristics in a test engine with those for blends of reference fuels of known cetane number under standard operating conditions. This is accomplished using the bracketing hand wheel procedure which varies the compression ratio (hand wheel reading) for the sample and each of the two bracketing reference fuels to obtain a specific ignition delay, thus permitting interpolation of cetane number in terms of hand wheel reading.

The cloud point, determined by the ASTM D2500 method, is the temperature at which a cloud of wax crystals appears when a lubricant or distillate fuel is cooled under standard conditions. Cloud point indicates the tendency of the material to plug filters or small orifices under cold weather conditions. The specimen is cooled at a specified rate and examined periodically. The temperature at which cloud is first observed at the bottom of the test jar is recorded as the cloud point. This test method covers only petroleum products and biodiesel fuels that are transparent in 40 mm thick layers, and with a cloud point below 49° C.

The aniline point, determined by the ASTM D611 method, is the lowest temperature at which equal volumes of aniline and hydrocarbon fuel or lubricant base stock are completely miscible. A measure of the aromatic content of a hydrocarbon blend is used to predict the solvency of a base stock or the cetane number of a distillate fuel. Specified volumes of aniline and sample, or aniline and sample plus n-heptane, are placed in a tube and mixed mechanically. The mixture is heated at a controlled rate until the two phases become miscible. The mixture is then cooled at a controlled rate and the temperature at which two separate phases are again formed is recorded as the aniline point or mixed aniline point.

The flash point, determined by ASTM D56, D92, D93 methods, is the minimum temperature at which a fluid will support instantaneous combustion (a flash) but before it will burn continuously (fire point). Flash point is an important indicator of the fire and explosion hazards associated with a petroleum product.

The octane number, determined by the ASTM D2699 or D2700 methods, is a measure of a fuel's ability to prevent detonation in a spark ignition engine. Measured in a standard single-cylinder; variable-compression-ratio engine by comparison with primary reference fuels. Under mild conditions, the engine measures research octane number (RON), while under severe conditions, the engine measures motor octane number (MON). Where the law requires posting of octane numbers on dispensing pumps, the antiknock index (AKI) is used. This is the arithmetic average of RON and MON, (R+M)/2. It approximates the road octane number, which is a measure of how an average car responds to the fuel.

New rapid, and direct methods to help better understand crude oil compositions and properties from analysis of whole crude oil will save producers, marketers, refiners and/or other crude oil users substantial expense, effort and time. Therefore, a need exists for an improved system and method for determining indicative properties of crude oil fractions from different sources.

SUMMARY

Systems and methods are disclosed for providing virtual assays including assigned assay values pertaining to an oil sample subject to analysis, and its fractions, based on data obtained by analytic characterization of the oil sample without fractionation, and the density of the oil sample. The virtual assay of the oil sample provides a full range of information about fractions of the oil sample including naphtha, gas oil, vacuum gas oil, residue, and other information about the properties of the oil sample. This virtual assay is useful for producers, refiners, and marketers to benchmark the oil quality and, as a result, evaluate the oils without performing the customary extensive and time-consuming crude oil assays.

In an embodiment, the present disclosure is directed to a method for producing a virtual assay of an oil sample, wherein the oil sample is characterized by a density, selected from the group consisting of crude oil, bitumen and shale oil, and characterized by naphtha, gas oil, vacuum gas oil and vacuum residue fractions. Nuclear magnetic resonance (NMR) spectroscopy data indicative of aromatic content, and optionally one or both of paraffinic and naphthenic content, of the oil sample, obtained by NMR spectroscopy of a solution of the oil sample, without distillation, in an NMR spectroscopy solvent, is entered into a computer. Virtual assay data of the oil sample and the naphtha, gas oil, vacuum gas oil and vacuum residue fractions is calculated and assigned as a function of the aromatic content, and optionally one or both of paraffinic and naphthenic content, and the density of the oil sample. The virtual assay data comprises a plurality of assigned data values.

In certain embodiments, the virtual assay data comprises: a plurality of assigned assay data values pertaining to the oil sample including one or more of the aromatic content, C5-asphaltenes content, elemental compositions of sulfur and nitrogen, micro-carbon residue content, total acid number and viscosity, a plurality of assigned assay values pertaining to the vacuum residue fraction of the oil sample including one or more of the elemental composition of sulfur and micro-carbon residue content; a plurality of assigned assay values pertaining to the vacuum gas oil fraction of the oil sample including one or both of the elemental compositions of sulfur and nitrogen; a plurality of assigned assay values pertaining to the gas oil fraction of the oil sample including one or more of the elemental compositions of sulfur and nitrogen, viscosity, and indicative properties including aniline point, cetane number, cloud point and/or pour point; and a plurality of assigned assay values pertaining to the naphtha fraction of the oil sample including one or more of the aromatic content, elemental composition of hydrogen and/or sulfur, paraffin content and octane number.

In certain embodiments, the virtual assay data also comprises: yields of fractions from the oil sample as mass fractions of boiling point ranges, including one or more of naphtha, gas oil, vacuum gas oil and vacuum residue; composition information of hydrogen sulfide and/or mercaptans in the oil sample and/or its fractions; elemental compositions of one or more of carbon, hydrogen, nickel, and vanadium; physical properties of the oil sample and/or its fractions including one or more of API gravity and refractive index; and/or indicative properties of the oil sample and/or its fractions including one or more of flash point, freezing point and smoke point.

In certain embodiments, the nuclear magnetic resonance spectrometer employs $^1H$ active nuclei to derive the aromatic content, and optionally one or both of paraffinic and naphthenic content. In some embodiments, the nuclear magnetic resonance spectrometer employs $^{13}C$ active nuclei to derive the aromatic content, and optionally one or both of paraffinic and naphthenic content.

In certain embodiments, each assay value is determined by a multi-variable polynomial equation with predetermined constant coefficients developed using linear regression techniques, wherein corresponding variables are the aromatic content, and optionally one or both of paraffinic and naphthenic content, and the density of the oil sample.

In an embodiment, the present disclosure is directed to a system for producing a virtual assay of an oil sample, wherein the oil sample is characterized by a density, is selected from the group consisting of crude oil, bitumen and shale oil, and is characterized by naphtha, gas oil, vacuum gas oil and vacuum residue fractions. The system comprises a nuclear magnetic resonance (NMR) spectrometer that outputs NMR spectroscopy data, a non-volatile memory device, a processor coupled to the non-volatile memory device, and a calculation module that is stored in the non-volatile memory device and that is executed by the processor. The non-volatile memory device stores the calculation module and data, the data including the NMR spectroscopy data that is indicative of aromatic content, and optionally one or both of paraffinic and naphthenic content, of the oil sample. The NMR spectroscopy data is obtained by NMR spectroscopy of the oil sample, obtained by NMR spectroscopy of a solution of the oil sample, without distillation, in an NMR spectroscopy solvent. The calculation module contains suitable instructions to calculate, as a function of the aromatic content (and optionally one or both of paraffinic and naphthenic content), and the density of the oil sample, a plurality of assigned data values as the virtual assay pertaining to the overall oil sample, and the naphtha, gas oil, vacuum gas oil and vacuum residue fractions of the oil sample.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF THE DRAWINGS

FIG. 2A is a graphic plot of depicts a graphical plot of typical NMR spectroscopy data of peaks (y-axis) against chemical shift (ppm, x-axis) based on $^1$H NMR spectra for the oil sample under investigation in the example herein.

DETAILED DESCRIPTION

Figure 1:
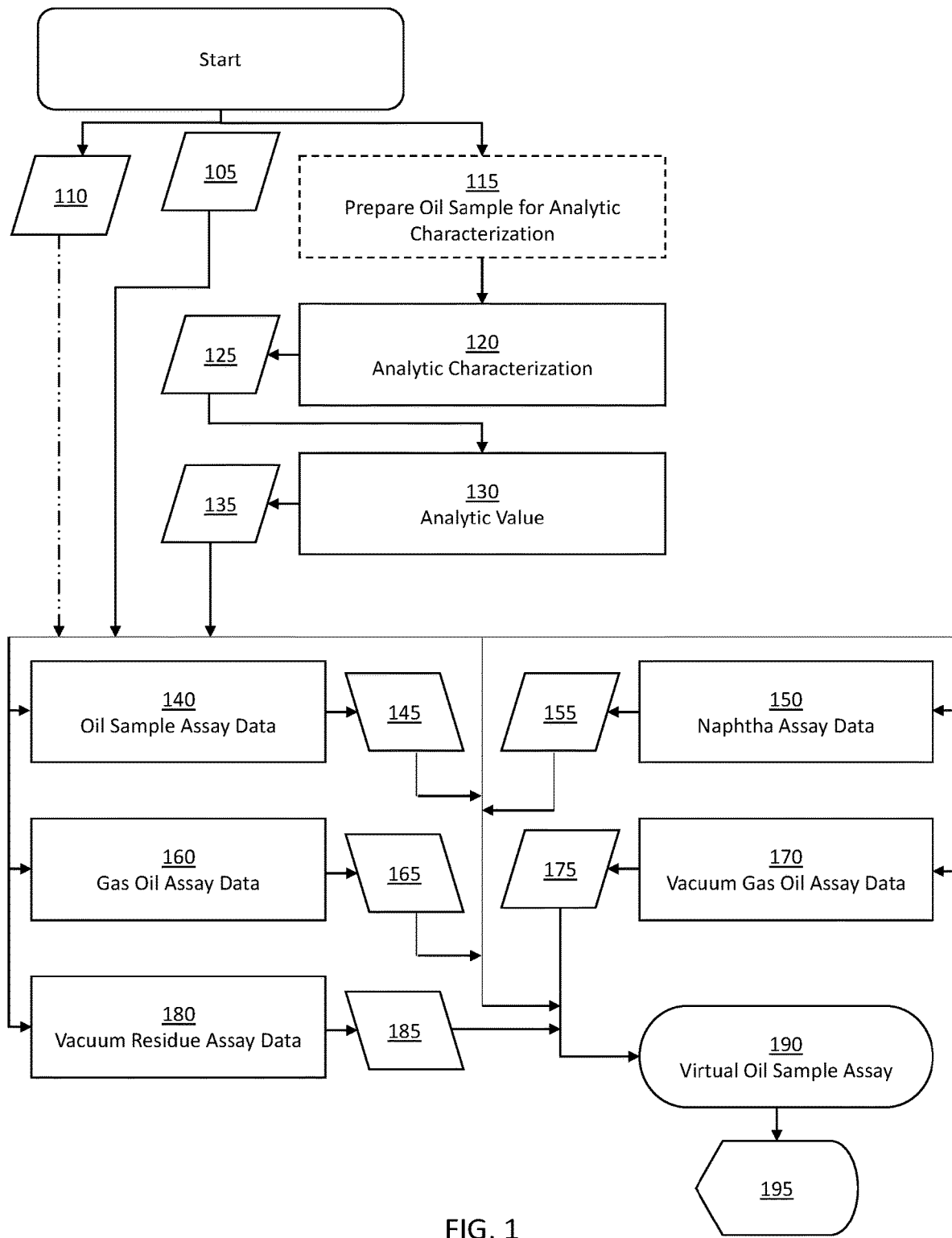
FIG. 1 is process flow diagram of steps used to implement the method described herein for providing virtual assays of an oil sample such as crude oil based on nuclear magnetic resonance (NMR) spectroscopy.

Systems and methods are disclosed for providing virtual assays of an oil sample such as crude oil based on nuclear magnetic resonance (NMR) spectroscopy carried out on the oil sample, and the density of the oil sample. The virtual assay provides a full range of information about fractions of the oil sample including naphtha, gas oil, vacuum gas oil, vacuum residue, and other information about the properties of the oil sample. Using the system and method herein, the virtual assay data pertaining to these several fractions of the oil sample and the oil sample itself is obtained without fractionation of the oil sample into the several components.

Concerning the naphtha fraction, assigned assay values for the virtual assay include: elemental composition values included in the virtual assay comprise one or more of hydrogen content, aromatic content, paraffin content and sulfur content; and an indicative property included in the virtual assay comprises an octane number. Concerning the gas oil fraction, assigned assay values for the virtual assay include: elemental composition values included in the virtual assay comprise one or more of sulfur content and nitrogen content; physical properties included in the virtual assay comprises viscosity and pour point; and indicative properties included in the virtual assay comprise one or more of aniline point, cetane number and cloud point. Concerning the vacuum gas oil fraction, assigned assay values for the virtual assay include: elemental composition values included in the virtual assay comprise one or more of sulfur content, nitrogen content and micro carbon residue content. Concerning the vacuum residue, assigned assay values for the virtual assay include: elemental composition values included in the virtual assay comprise one or more of sulfur content and micro carbon residue content. Concerning the full range of the oil sample, assigned assay values for the virtual assay include: elemental composition values included in the virtual assay comprise one or more of asphaltene content, sulfur content, nitrogen content and total acids content (total acid number, mg KOH/100 g); and physical properties included in the virtual assay comprises viscosity and pour point.

In certain embodiments of the virtual assay provided herein, the "naphtha fraction" refers to a straight run fractions from atmospheric distillation containing hydrocarbons having a nominal boiling range of about 20-205, 20-193, 20-190, 20-180, 20-170, 32-205, 32-193, 32-190, 32-180, 32-170, 36-205, 36-193, 36-190, 36-180 or 36-170° C.; the "gas oil fraction" refers to a straight run fractions from atmospheric distillation containing hydrocarbons having a nominal boiling range of about 170-400, 170-380, 170-370, 170-360, 180-400, 180-380, 180-370, 180-360, 190-400, 190-380, 190-370, 190-360, 193-400, 193-380, 193-370 or 193-360° C.; the "vacuum gas oil fraction" refers to a straight run fractions from vacuum distillation containing hydrocarbons having a nominal boiling range of about 360-565, 360-550, 360-540, 360-530, 360-520, 360-510, 370-565, 370-550, 370-540, 370-530, 370-520, 370-510, 380-565, 380-550, 380-540, 380-530, 380-520, 380-510, 400-565, 400-550, 400-540, 400-530, 400-520 or 400-510° C.; and "vacuum residue" refers to the bottom hydrocarbons from vacuum distillation having an initial boiling point corresponding to the end point of the VGO range hydrocarbons, for example about 510, 520, 530, 540, 550 or 565° C., and having an end point based on the characteristics of the crude oil feed.

The system and method is applicable for naturally occurring hydrocarbons derived from crude oils, bitumens or shale oils, and heavy oils from refinery process units including hydrotreating, hydroprocessing, fluid catalytic cracking, coking, and visbreaking or coal liquefaction. Samples can be obtained from various sources, including an oil well, core cuttings, oil well drilling cuttings, stabilizer, extractor, or distillation tower. In certain embodiments system and method is applicable for crude oil, whereby a virtual assay is obtained using the systems and methods herein without the extensive laboratory work required for distillation and analysis of each of the individual fractions.

Referring to FIG. 1, a process flow diagram of steps carried out to obtain a virtual assay 195 is provided. Prior to carrying out the steps outlined in FIG. 1, a set of constants is obtained for each of the elemental composition values/physical properties/indicative properties to be calculated using the process and system disclosed herein to obtain a virtual assay, represented as dataset 105. The set of constants can be developed, for instance by linear regression techniques, based on empirical data of a plurality of crude oil assays and analyses using conventional techniques including distillation and industry-established testing methods to obtain the crude oil assay data. Examples of sets of constants used for calculating assigned assay values to produce the virtual assay 195 based on various analytic characterization techniques are provided herein.

At step 110, the density of the oil sample is provided (steps for obtaining this density are not shown and can be carried out as is known, in certain embodiments a 15° C./4° C. density in units of kilograms per liter using the method described in ASTM D4052); this density value can be stored in memory with other data pertaining to the oil sample, or conveyed directly to the one or more steps as part of the functions thereof. In step 115, if necessary, the oil sample is prepared for a particular analytic characterization technique (shown in dashed lines as optional). In step 120, analytic characterization of the oil sample, or the oil sample prepared as in step 115, without fractionation, is carried out. As a result, analytic characterization data 125 is obtained.

In step 130, the analytic characterization data 125 is used to calculate one or more analytical values 135, which are one common analytical value or a common set of analytical values used in subsequent steps to calculate a plurality of different elemental composition values/physical properties/indicative properties that make up the virtual assay. In the embodiments herein the one common analytical value or common set of analytical values includes one or more of the aromatic content of the oil sample, the paraffinic content of the oil sample, and/or the naphthenic content of the oil sample.

Steps 140, 150, 160, 170 and 180 are used to calculate and assign a plurality of different elemental composition values/physical properties/indicative properties that make up the virtual assay 195, for each of a total oil sample, a naphtha fraction, a gas oil fraction, a vacuum gas oil fraction and a vacuum residue fraction, respectively. Each of the steps produces corresponding assigned assay values for the virtual assay 195, including assigned assay values 145 pertaining to the total oil sample, assigned assay values 155 pertaining to a naphtha fraction, assigned assay values 165 pertaining to a gas oil fraction, assigned assay values 175 pertaining to a vacuum gas oil fraction and assigned assay values 185 pertaining to a vacuum residue fraction.

In certain embodiments, the steps are carried out in any predetermined sequence, or in no particular sequence, depending on the procedures in the calculation modules. In certain embodiments, the steps are carried out in parallel. The process herein uses a common analytical value, or set of analytical values, in conjunction with the set of constants and the density of the oil sample, for each of the assigned assay values (elemental composition values/physical properties/indicative properties) in the given virtual oil sample assay 195 produced at step 190. For instance, each of the steps 140, 150, 160, 170 and 180 are carried in any sequence and/or in parallel out as show using the equations herein for various analytical values or sets of analytical values.

The assigned assay values from each of the fractions and the total oil sample are compiled and presented as a virtual assay 195, which can be, for instance, printed or rendered on a display visible to, or otherwise communicated to, a user to understand the composition and properties of the crude. With the virtual assay 195, users such as customers, producers, refiners, and marketers can benchmark the oil quality. The virtual assay 195 can be used to guide decisions related to an appropriate refinery or refining unit, for processing the oil from which the oil sample is obtained, and/or for processing one or more of the fractions thereof. In addition the assigned assay values including the indicative properties are used to determine the engine/fuel performance or usability or flow characteristic or composition. This can be accomplished using the method and system herein without performing the customary extensive and time-consuming crude oil assays.

The assigned assay values for the virtual assay herein are calculated as a function of one or more analytical values, and the density of the oil sample, as denoted at (1).

$$AD = f(\rho, AV) \quad (1)$$

where:
AD is the assigned assay value (for example a value and/or property representative of an elemental composition value, a physical property or an indicative property);
AV is an analytical value of the oil sample, wherein AV can be a single analytical value, or wherein AV can be AV(1) ... AV(n) as plural analytical values of the oil sample, wherein n is an integer of 2 or more, in certain embodiments 2, 3 or 4; and
$\rho$ is the density of the oil sample, in certain embodiments a 15° C./4° C. density in units of kilograms per liter using the method described in ASTM D4052.

In certain embodiments an analytical value is a single AV, that is one of the aromatic, naphthenic or paraffinic carbon content of the oil sample, for example as determined by NMR spectrometry carried out on the oil sample. In further embodiments a set of analytical values includes AV(1) ... AV(n) and represents two or more of aromatic, naphthenic and paraffinic carbon content of the oil sample, for example as determined by NMR spectrometry carried out on the oil sample. Advantageously, the method and system herein deploy analytical characterization by NMR spectroscopy to carry out analysis of the oil sample without fractionating, obtain an analytical value or set of analytical values based on the NMR spectroscopy analysis of the oil sample, and use the analytical value or set of analytical values, and the density of the oil sample, to obtain a plurality of assigned assay values (for example a value and/or property representative of an elemental composition value, a physical property or an indicative property) to produce a virtual assay of the oil sample. The NMR spectroscopy can include one or both of $^1$H NMR spectroscopy and/or $^{13}$C NMR spectroscopy as described herein.

In one embodiment, an assigned assay value is calculated using a third degree multi variable polynomial equation including the analytical value, the density of the oil sample, and a plurality of constants, for example predetermined by linear regression, as denoted in equation (2a).

$$AD = K_{AD} + X1_{AD}*AV + X2_{AD}*AV2 + X3_{AD}*AV3 + X4_{AD}*\rho*AV \quad (2a)$$

where:
AD is the assigned assay value (for example a value and/or property representative of an elemental composition value, a physical property or an indicative property);
AV is an analytical value of the oil sample;
$\rho$ is the density of the oil sample, in certain embodiments a 15° C./4° C. density in units of kilograms per liter using the method described in ASTM D4052; and
$K_{AD}$, $X1_{AD}$, $X2_{AD}$, $X3_{AD}$, and $X4_{AD}$ are constants, for instance, developed using linear regression techniques (note that in certain embodiments and for certain assigned assay values, one or more of $K_{AD}$, $X1_{AD}$, $X2_{AD}$, $X3_{AD}$ and $X4_{AD}$ is/are not used, or is/are zero).

In another embodiment, an assigned assay value is calculated using a third degree multi variable polynomial equation including the analytical value, the density of the oil sample, and a plurality of constants, for example predetermined by linear regression, as denoted in equation (2b).

$$AD = K_{AD} + X1_{AD}*\rho + X2_{AD}*\rho^2 + X3_{AD}*\rho^3 + X4_{AD}*AV + X5_{AD}*AV^2 + X6_{AD}*AV^3 + X7_{AD}*\rho*AV \quad (2b)$$

where:
AD is the assigned assay value (for example a value and/or property representative of an elemental composition value, a physical property or an indicative property);
AV is an analytical value of the oil sample;
$\rho$ is the density of the oil sample, in certain embodiments a 15° C./4° C. density in units of kilograms per liter using the method described in ASTM D4052; and
$K_{AD}$, $X1_{AD}$, $X2_{AD}$, $X3_{AD}$, $X4_{AD}$, $X5_{AD}$, $X6_{AD}$ and $X7_{AD}$ are constants, for instance, developed using linear regression techniques (note that in certain embodiments and for certain assigned assay values, one or more of $K_{AD}$, $X1_{AD}$, $X2_{AD}$, $X3_{AD}$, $X4_{AD}$, $X5_{AD}$, $X6_{AD}$ and $X7_{AD}$ is/are not used, or is/are zero).

Assigned assay values that can be determined and included for display or presentation to the user in the virtual assay produced using the systems and methods herein include one or more of:
elemental composition of the oil sample and its fractions including the sulfur and nitrogen compositions;
TAN (total acid number) of the oil sample;

composition of certain desirable and undesirable compounds or types of compounds present in the oil sample and/or its fractions, including one or more of, micro carbon residue, C5-asphaltenes (the yield of asphaltenes using separation based on C5 paraffins as deasphalting solvent), paraffins, aromatics, and naphthenes;

physical properties of the oil sample and/or its fractions including viscosity such as kinematic viscosity;

indicative properties of the oil sample and/or its fractions, including one or more of cloud point, pour point, research octane number, cetane number and aniline point.

In certain embodiments, the assigned assay values can include yields of fractions from the oil sample, for example as mass fractions of boiling point ranges, including one or more of naphtha, gas oil, vacuum gas oil and vacuum residue. In certain embodiments, the assigned assay values can include composition information of hydrogen sulfide and/or mercaptans in the oil sample and/or its fractions. In certain embodiments, the assigned assay values can include elemental compositions of one or more of carbon, hydrogen, nickel, and vanadium. In certain embodiments, the assigned assay values can include physical properties of the oil sample and/or its fractions including one or more of API gravity and refractive index. In certain embodiments, the assigned assay values can include indicative properties of the oil sample and/or its fractions including one or more of flash point, freezing point and smoke point.

In certain embodiments, a method for producing a virtual assay of an uncharacterized oil sample is provided. The uncharacterized oil sample is characterized by a density, selected from the group consisting of crude oil, bitumen and shale oil, and characterized by naphtha, gas oil, vacuum gas oil and vacuum residue fractions. The virtual assay comprises a plurality of assigned data values. The uncharacterized oil sample is obtained, for instance the sample being between one to two milliliters in volume and not subject to any fractionation. A plurality of known data values (corresponding to the assigned data values used in the virtual assay) for known oil samples with known densities (which known oil samples exclude the uncharacterized oil sample) are obtained. This data is obtained from empirical data of a plurality of existing crude oil assays and/or analyses using conventional techniques including distillation and industry-established testing methods. One or more selected analytical techniques are carried out on the each of the known oil samples, and one or more analytical values are calculated for each of the known oil samples. The one or more selected analytical techniques are carried out on the uncharacterized oil sample, and one or more analytical values are calculated for the uncharacterized oil sample. Constants of a polynomial equation are obtained, and the polynomial equation is used to determine a plurality of assigned data values that make up the virtual assay of the uncharacterized oil sample. The polynomial equation is a function of density and the one or more analytical values of the uncharacterized oil sample. The constants of the polynomial equation are determined using a fitting method to fit the plurality of known data values of the plurality of known oil samples to the plurality of values of the density of the plurality of known oil samples and the plurality of the one or more analytical values for the plurality of known oil samples.

Rather than relying on conventional techniques including distillation and laborious, costly and time-consuming analytical methods to measure/identify data regarding the crude oil and/or its fractions including elemental composition, physical properties and indicative properties, as little as 1 gram of oil can be analyzed. From the analysis of a relatively small quantity of the oil sample, the assigned assay values are determined by direct calculation, without requiring distillation/fractionization.

NMR spectroscopy is the analytic characterization technique that is employed on a relatively small quality of an oil sample, such as crude oil. The analytic characterization system and corresponding technique is carried out using the full range of the oil sample, without fractionating. An analytical value, or set of analytical values, comprising or consisting of one or more of the aromatic, naphthenic or paraffinic carbon content of the oil sample obtained from said analytic characterization technique, is used to calculate and assign physical and indicative properties that are the requisite data for the virtual oil sample assay. The method and system provides insight into the properties of oil sample, the naphtha fraction, the gas oil fraction, the vacuum gas oil fraction, and the vacuum residue fraction, without fractionation/distillation (conventional crude oil assays). The virtual oil sample assay will help producers, refiners, and marketers benchmark the oil quality and, as a result, evaluate (qualitatively and economically) the oils without going thru costly and time consuming crude oil assays. Whereas a conventional crude oil assay method could take up to two months, the method and system herein can provide a virtual assay in less than one day and in certain embodiments less than 1-2 hours. In addition, the method and system herein carried out at 1% or less of the cost of a traditional assay requiring distillation/fractionization follows by individual testing for each type of property and for each fraction.

The systems and methods herein are implemented using an analytical value, or set of analytical values, derived from NMR spectroscopy data, as an analytical value in equations (1), and (2a) or (2b), above. Embodiments of such methods are described in the context of assigning an indicative property to a fraction of an oil sample in commonly owned U.S. Pat. No. 10,684,239B2, which is incorporated by reference herein in its entirety. In the systems and methods herein, and with reference to FIG. 1, a virtual assay 195 of an oil sample is obtained at step 190, wherein each assigned data value of the virtual assay is a function of the NMR spectroscopy measurement of the oil sample, or in another embodiment as a function of the NMR spectroscopy measurement of the oil sample and the density of the oil sample. The virtual assay provides information about the oil sample and individual fractions thereof to help producers, refiners, and marketers benchmark the oil quality and, as a result, evaluate the oils without performing the customary extensive and time-consuming crude oil assays involving fractionation/distillation and several individual and discrete tests.

The oil sample is prepared, step 115, by dissolving the oil sample in a suitable solvent for NMR spectroscopy. For example, a small quantity (for instance, about 5-25 mg of the oil sample for $^1$H NMR spectroscopy, or about 50-100 mg of the oil sample for $^{13}$C NMR spectroscopy) of an oil sample is dissolved in an effective quantity of a suitable NMR spectroscopy solvent, such as 0.5-5, 0.5-2 or 0.5-1.5 ml of deuterated solvents such as chloroform-D, acetone-D6, benzene-D6, deuterium oxide (D20), DMSO-D6, ethanol-D6 and/or methanol-D4, or other solvent known in NMR spectroscopy, to form a solution that is in the range of about 20-50, 30-50 35-50 or 35-45% w/v (grams of solute per 100 milliliters of solution).

The solution is analyzed, step 120, and the NMR spectrum is obtained. Step 120 is carried out and the analytic characterization data, the NMR spectrum, is entered into the computer system 400 described herein with respect to FIG. 4, for example stored into non-volatile memory of the data storage memory 480, represented as the analytic characterization data 125. This can be carried out by a raw data receiving module stored in the program storage memory 470.

One or more analytical values are obtained, step 130, from the spectrum. The analytical values obtained from NMR spectroscopy data include the aromatic content, the naphthenic content and the paraffinic content of the oil sample. Step 130 is carried out, for example, by execution by the processor 420 of one or more modules stored in the program storage memory CS70, and the analytical value or set of analytical values 135, which is one or more of the aromatic content, the naphthenic content and/or the paraffinic content of the oil sample, are stored in the program storage memory 470 or the data storage memory 480, for use in the modules determining the assigned data values. In certain embodiments, the density of the oil sample, provided at step 110, is stored in the program storage memory 470 or the data storage memory 480, for use in the modules determining the assigned data values; this can be carried out by a raw data receiving module stored in the program storage memory 470.

The assigned data values including virtual assay data 145 pertaining to the total oil sample, virtual assay data 155 pertaining to a naphtha fraction, virtual assay data 165 pertaining to a gas oil fraction, virtual assay data 175 pertaining to a vacuum gas oil fraction and virtual assay data 185 pertaining to a vacuum residue fraction, are obtained according to the functions described herein, for example, in the corresponding steps 140, 150, 160, 170 and 180. The constants used for determining the assigned data values, are provided at step 105 and are stored in the program storage memory 470 or the data storage memory 480, for use in the modules determining the assigned data values. The steps for obtaining the assigned data values are carried out, for example, by execution by the processor 420 of one or more modules stored in the program storage memory 470, and the several assigned data values are calculated and stored in the data storage memory 480, presented on the display 410 and/or presented to the user by some other output device such as a printer.

NMR spectra are obtained by a suitable known or to be developed nuclear magnetic resonance spectrometer. NMR is a property that magnetic nuclei have under a magnetic field and applied electromagnetic (EM) pulse or pulses, which causes the nuclei to absorb energy from the EM pulse and radiate this energy back out. The energy radiated back out is at a specific resonance frequency which depends on the strength of the magnetic field and other factors. This allows the observation of specific quantum mechanical magnetic properties of an atomic nucleus. Many scientific techniques exploit NMR phenomena to study molecular physics, crystals and non-crystalline materials through NMR spectroscopy. NMR spectroscopy is a technique which exploits the magnetic properties of certain nuclei.

All stable isotopes that contain an odd number of protons and/or of neutrons have an intrinsic magnetic moment and angular momentum, in other words a nonzero spin, while all nuclides with even numbers of both have spin 0. The most commonly studied nuclei are $^1$H (the most NMR-sensitive isotope after the radioactive $^3$H) and $^{13}$C, although nuclei from isotopes of many other elements (e.g. $^2$H, $^{10}$B, $^{11}$B, $^{14}$N, $^{15}$N, $^{17}$O, $^{19}$F, $^{23}$Na, $^{29}$Si, $^{31}$P, $^{35}$Cl, $^{113}$Cd, $^{129}$Xe, $^{195}$Pt) are studied by high-field NMR spectroscopy as well.

NMR is a technique for determining the structure of organic compounds. NMR is non-destructive, and with modern instruments good data can be obtained from samples weighing less than a milligram. When a sample is placed in a magnetic field, NMR active nuclei (such as $^1$H or $^{13}$C) absorb at a frequency characteristic of the isotope. The resonant frequency, energy of the absorption and the intensity of the signal are proportional to the strength of the magnetic field. For example, in a 21 tesla magnetic field, protons resonate at 900 MHz. It is common to refer to a 21 T magnet as a 900 MHz magnet, although different nuclei resonate at a different frequency at this field strength.

In one embodiment, the determination of the assigned data is carried out using variables comprising or consisting of: a compositional quantity of the oil sample, as determined by a $^{13}$C NMR spectra of the oil sample, such as one or more of the aromatic content of the oil sample, the paraffinic content of the oil sample, and/or the naphthenic content of the oil sample; and the density of the oil sample. In another embodiment, the determination of the assigned data is carried out using variables comprising or consisting of the aromatic content of the oil sample, as determined by a $^1$H NMR spectra of the oil sample, and the density of the oil sample. This determination is, for example, represented as step 110 in FIG. 1.

$$AD = f(\rho, C_A) \quad (3)$$

where:
AD is the assigned data value (for example a value and/or property representative of an elemental composition value, a physical property or an indicative property);
$C_A$ = aromatic content of the oil sample as determined by NMR spectroscopy, for instance $^{13}$C NMR or $^1$H NMR; and
$\rho$ is the density of the oil sample, in certain embodiments a 15° C./4° C. density in units of kilograms per liter using the method described in ASTM D4052.

For example, this relationship can be expressed as follows:

$$AD = K_{AD} + X1_{AD} * \rho + X2_{AD} * \rho^2 + X3_{AD} * \rho^3 + \quad (4)$$
$$X4_{AD} * C_A + X5_{AD} * C_A^2 + X6_{AD} * C_A^3 + X7_{AD} * \rho * C_A$$

where AD, $C_A$ and $\rho$ are as in equation (3), and where:
$K_{AD}$, $X1_{AD}$, $X2_{AD}$, $X3_{AD}$, $X4_{AD}$, $X5_{AD}$, $X6_{AD}$ and $X7_{AD}$ are constants, for instance, developed using linear regression techniques, for each AD to be determined (note that in certain embodiments and for certain assigned assay values, one or more of $K_{AD}$, $X1_{AD}$, $X2_{AD}$, $X3_{AD}$, $X4_{AD}$, $X5_{AD}$, $X6_{AD}$ and $X7_{AD}$ is/are not used, or is/are zero).

Using the equation (4), one or more assigned data values AD are determined using the analytical value $C_A$ as determined by a $^{13}$C NMR or $^1$H NMR spectra of the oil sample, and the density of the oil sample. Note that in equation (4), an analytical value $C_A$ is used representative of the aromatic content of the oil sample, the desired AD values can also be obtained using the paraffinic content of the oil sample ($C_P$) or the naphthenic content of the oil sample ($C_N$). Further, it is possible to obtain the desired AD values using a combination of two or more of $C_A$, $C_P$ or $C_N$.

Tables 3A and 3B list assigned data for a virtual assay of an oil sample under investigation, with descriptions, abbreviations and units, for each assigned data property for the naphtha fraction, the gas oil fraction, the vacuum gas oil fraction, the vacuum residue fraction and the overall oil sample. Tables 3A and 3B further provide exemplary constants, for instance, developed using linear regression techniques, for plural assigned data values to be determined based on the density of the oil sample and either $^{13}$C NMR spectra data related to the oil sample (Table 3A) or $^{1}$H NMR spectra data related to the oil sample (Table 3B). These constants are used in the Examples 1 and 2 below with the calculated values provided in Tables 4A and 4B compared to the actual values as determined by a conventional crude oil assay. Note that constants can also be developed in embodiments in which $C_P$, $C_N$, or a combination of two or more of $C_A$, $C_P$ or $C_N$ are used as the analytical value(s).

The constants, for example as in Tables 3A and/or 3B, are stored as in step 105 in the process flow diagram of FIG. 1. These are used in one or more calculation modules to obtain the virtual assay 195 of an oil sample as in step 190, in conjunction with the analytical values obtained in step 130 from the NMR spectroscopy data obtained in step 120, the aromatic content, and optionally one or more of the naphthenic or paraffinic content, of the oil sample. In certain embodiments the constants are stored as in step 105, and the density is stored as in step 110; the constants are used in one or more calculation modules to obtain the virtual assay 195 of an oil sample as in step 190, in conjunction with density of the oil sample stored in step 110 and the analytical values obtained in step 130 from the NMR spectroscopy data obtained in step 120. As shown and described, modules are separated based on the fraction for which assigned data values are obtained, but is it understood that they can be arranged in any manner so as to provide all of the assigned data values required for the virtual assay of the oil sample.

In certain embodiments, the assigned data values include virtual assay data 145 pertaining to the total oil sample, virtual assay data 155 pertaining to a naphtha fraction, virtual assay data 165 pertaining to a gas oil fraction, virtual assay data 175 pertaining to a vacuum gas oil fraction and virtual assay data 185 pertaining to a vacuum residue fraction. This data is obtained according to the function (3) described above (for example expressed as in equation (4) described above), for example, with the corresponding modules/steps 140, 150, 160, 170 and 180.

In certain embodiments, the analytical value or set of analytical values obtained as in step 130 is/are determined by identifying peaks of the spectra, and by integrating peaks under those spectra.

Example 1

Figure 2A:
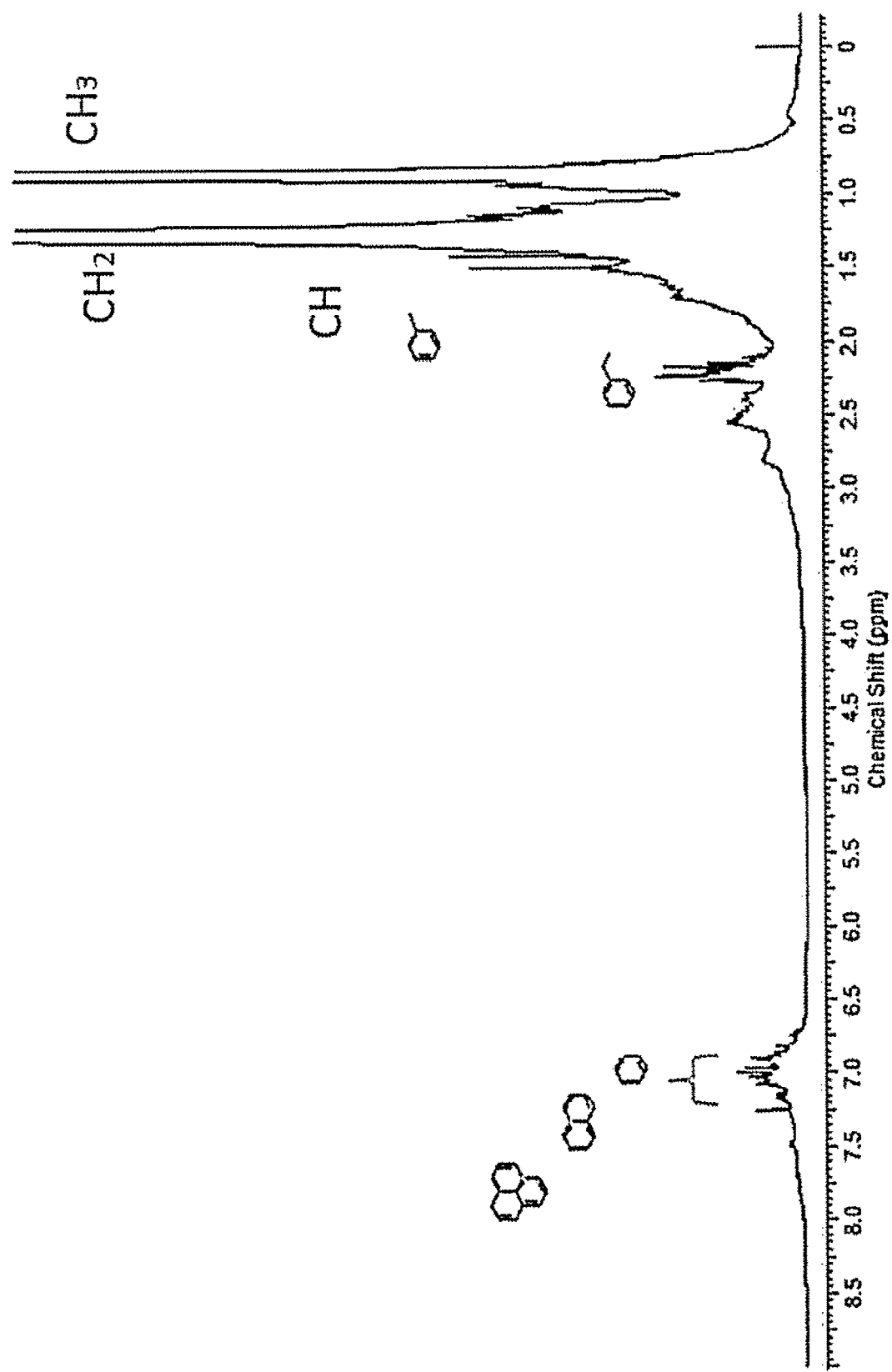
FIG. 2A is a graphic plot of depicts a graphical plot of typical NMR spectroscopy data of peaks (y-axis) against chemical shift (ppm, x-axis) based on $^{13}$C NMR spectra for the oil sample under investigation in the example herein.
Figure 3:
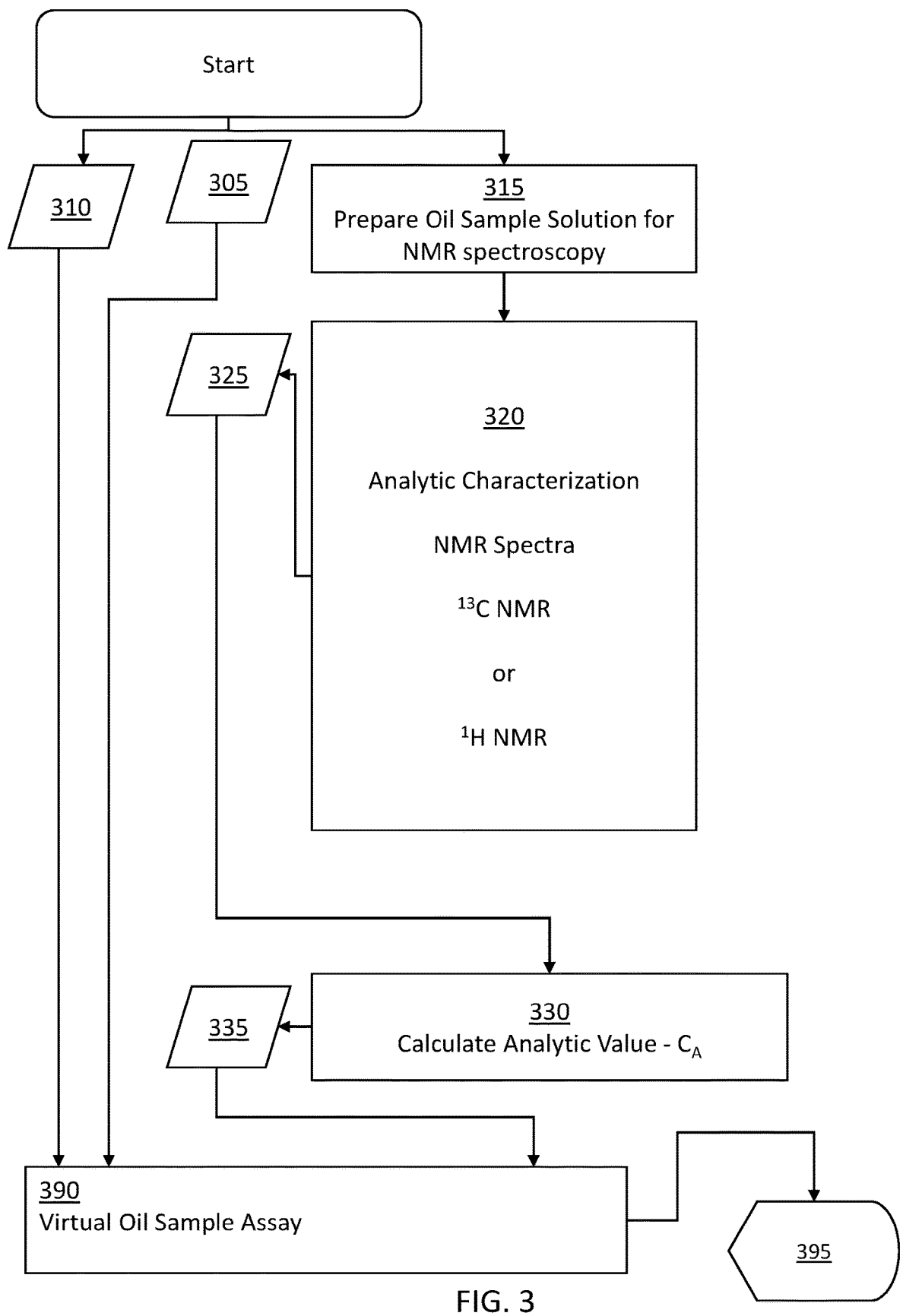
FIG. 3 is a process flow diagram of steps used in an example herein to provide a virtual assay of a crude oil sample based on NMR spectroscopy.

A crude oil sample, as the oil sample under investigation, was prepared into a solution and analyzed by $^{13}$C NMR spectrometry according to the methods described herein. FIG. 2A depicts a graphical plot of peaks (y-axis) against chemical shift (ppm, x-axis) based on $^{13}$C NMR spectra for the oil sample under investigation. FIG. 3 shows a process flow chart of steps for a method of obtaining a virtual oil sample assay based on NMR spectra data. In step 305, constants are obtained, for example corresponding to the data in Table 3A. In step 310, the density of the oil sample is obtained. In the Example 1, the oil sample is Arabian medium crude with a 15° C./4° C. density of 0.8828 Kg/L, determined using the method described in ASTM D4052. In step 315, the oil sample is prepared. The NMR experiments were carried out using 40% w/v sample solution (grams of solute per 100 milliliters of solution) using deuterated chloroform (99.8% D, Cambridge Isotope Laboratories Inc.) as solvent, with tetramethylsilane (TMS) used as an internal standard.

In step 320, analytic characterization of the oil sample prepared as in step 315, without fractionation, is carried out, obtaining $^{13}$C NMR spectra for an oil sample as shown in FIG. 2A; the data pertaining to this spectrum is obtained and stored as the analytic characterization data in step 325. In the Example 1, the quantitative NMR spectra were recorded at room temperature on a Varian VNMS 500 NMR spectrometer operating at 125.67 MHz for $^{13}$C using Dual Broadband SW/PFG probe with 5 mm 506-PP (Wilmad Glass CO., Inc.) NMR sample tubes. $^{13}$C NMR was performed and an inverse gated WALTZ-16 modulated decoupling mode was used to suppress nuclear Overhauser enhancement. The experimental parameters were: 30 degree pulse length of 2.7 us with a relaxation delay of 10 s, 1.69 s acquisition time, 128 K time domain data, 35878 Hz spectra width and typical 6000 repetitions were employed. Data was processed with 5 Hz line broadening.

In step 330, an analytical value is determined, based on aromatic carbons being identified on a different region of the spectra stored in step 325. The analytical value is stored at step 335. The amount of aromatic carbon was determined by integrating the peaks identified. The carbon types were determined in the spectrum as follows: Aromatic Region (165-100 ppm); Aliphatic Region (75-5 ppm). As for the paraffinic and naphthenic, the 75-5 ppm region of the spectrum can be used to define integrals wherever a paraffin resonance is found. In this area total paraffinic carbons can be determined. It is assumed that all narrow resonances are paraffinic, and that any obvious broader NMR peak groups that represent a superposition of narrow paraffinic resonances are 100% paraffinic. The naphthenic humps can be removed from the spectrum first to determine the paraffinic carbons. The difference between the total paraffinic carbon and the paraffinic carbon determined the total naphthenic carbon.

A sample of Arabian medium crude with a density of 0.8828 Kg/l (15° C./4° C. density using the method described in ASTM D4052) was analyzed by $^{13}$C NMR spectroscopy. The oil sample fractional weight composition is 0.279 naphthenic, 0.529 paraffinic, and 0.192 aromatic carbon. The aromatic carbon corresponds to the variable $C_A$ herein, determined at step 330, which in equation (4) herein is expressed as a weight percent, 19.2 W %.

The variable $C_A$, stored at step 335, is applied to step 390. At step 390, Equation (4) and the constants from Table 3A are applied for each of the listed ADs, using the variable $C_A$ stored at step 335, the constants stored at step 305, and the density of the oil sample stored at step 310, as shown below. Each of the determined ADs can be added to the virtual assay of the oil sample. For example, this can be carried out as one step, or as plural steps, for instance, similar to steps 140, 150, 160, 170 and 180 described herein in conjunction with FIG. 1 to calculate a plurality of different elemental composition values/physical properties/indicative properties that make up the virtual assay, for each of a total oil sample, a naphtha fraction, a gas oil fraction, a vacuum gas oil fraction and a vacuum residue fraction, respectively, and to produce the virtual oil sample assay 195 at step 190.

Equation (4) is applied to each of the ADs that make up the virtual assay including those identified in Table 3A, using the corresponding units. In addition, the constants denoted in Table 3A are used as the constants $K_{AD}$, $X1_{AD}$, $X2_{AD}$, $X3_{AD}$, $X4_{AD}$, $X5_{AD}$, $X6_{AD}$ and $X7_{AD}$) in equation (4); the value $C_A$, determined to be 19.2 W % based on the spectrum in FIG. 2A, is used in equation (4); and the density ρ used in equation (4) for the of the oil sample under investigation is the 15° C./4° C. density in units of kilograms per liter using the method described in ASTM D4052, which is 0.8828 Kg/L. The calculated AD values are provided for the oil sample under investigation in Table 4A, compared to the actual values obtained using a conventional crude oil assay.

Example 2

Figure 2B:
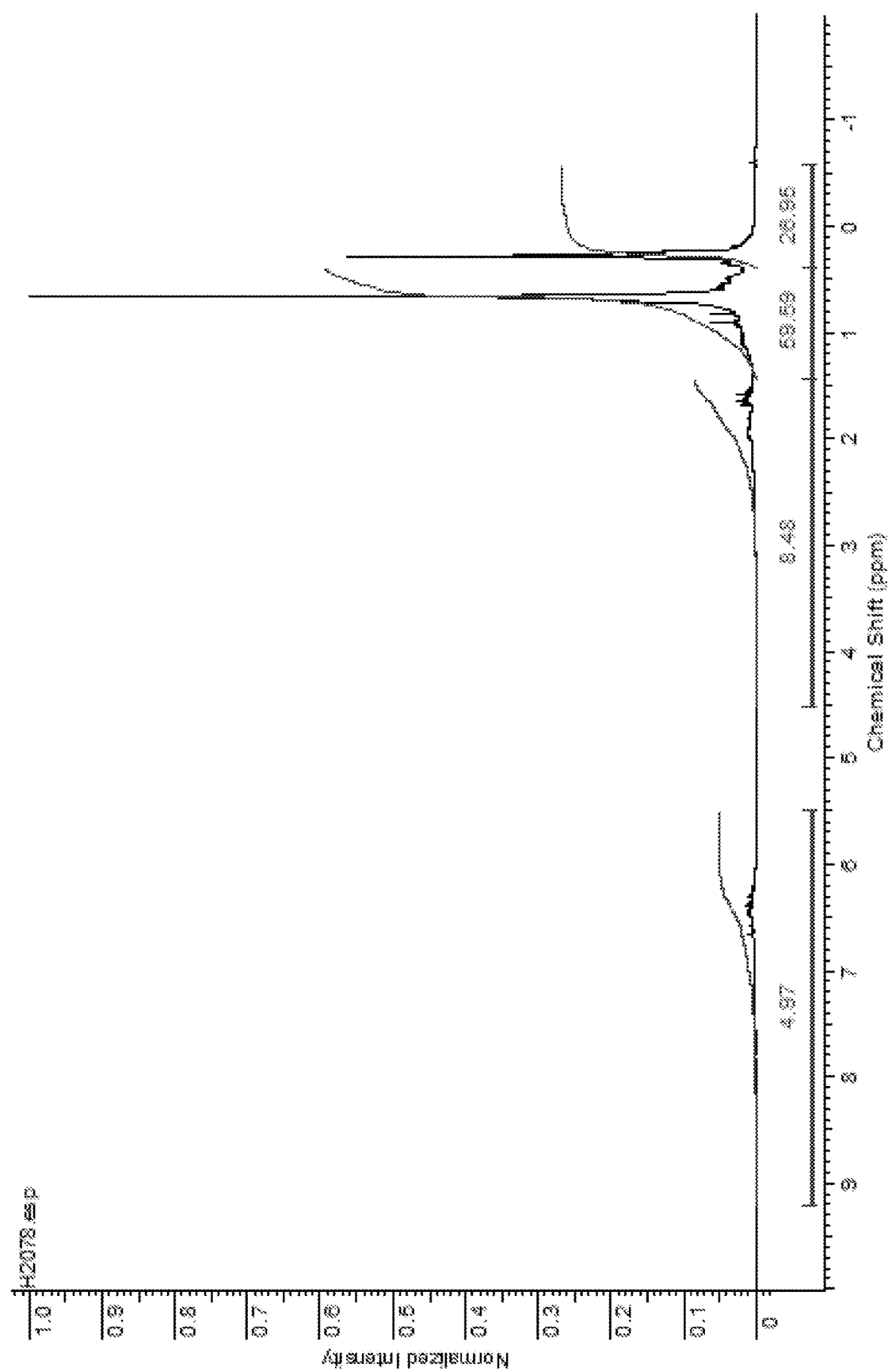

A crude oil sample, as the oil sample under investigation, was prepared into a solution and analyzed by $^1$H NMR spectrometry according to the methods described herein. FIG. 2B depicts a graphical plot of data peaks (y-axis) against chemical shift (ppm, x-axis) based on $^1$H NMR spectra for the oil sample under investigation. FIG. 3 shows a process flow chart of steps for a method of obtaining a virtual oil sample assay based on $^1$H NMR spectra data. In step 305, constants are obtained, for example corresponding to the data in Table 3B. In step 310, the density of the oil sample is obtained. In the Example 2, the oil sample is Arabian medium crude with a 15° C./4° C. density of 0.8828 Kg/L, determined using the method described in ASTM D4052. In step 315, the oil sample is prepared. The NMR experiments were carried out using 25% w/v sample solution (grams of solute per 100 milliliters of solution) using deuterated chloroform (99.8% D, Cambridge Isotope Laboratories Inc.) as solvent, with tetramethylsilane (TMS) used as an internal standard. In step 320, analytic characterization of the oil sample prepared as in step 315, without fractionation, is carried out, obtaining $^1$H NMR spectra for an oil sample as shown in FIG. 2B; the data pertaining to this spectrum is obtained and stored as the analytic characterization data in step 325. In the Example 2, the quantitative NMR spectra were recorded at room temperature on a Varian VNMS 500 NMR spectrometer operating at 499.78 MHz for $^1$H using Dual Broadband SW/PFG probe with 5 mm 506-PP (Wilmad Glass CO., Inc.) NMR sample tubes.

$^1$H NMR was performed using 16 scan numbers, 45 degree pulse length of 4.75 us, 5 s relaxation delay, 3 s acquisition time, 10 K time domain data, 15060 Hz spectra width and, 64 repetitions. The experimental parameters were: 30 degree pulse length of 2.7 s with a relaxation delay of 10 s, 1.69 s acquisition time, 128 K time domain data, 35878 Hz spectra width and typical 6000 repetitions were employed. Data was processed with 5 Hz line broadening.

In step 330, an analytical value is determined, based on aromatic carbons being identified on a different region of the spectra stored in step 325. The analytical value is stored at step 335. The paraffinic and aromatic hydrogens can be determined in the spectrum in the following regions as the analytical values, in step 330:

| Hydrogen Type | Shift in Spectrum |
| --- | --- |
| Methyl ($CH_3$) protons of alkyl chains (γ) or further from the aromatic ring or methyl protons ($CH_3$) of saturated compounds ($HS_{CH3}$). | 0.5-1.0 ppm |
| Methylene ($CH_2$) and methane (CH) protons of alkyl chains (β) or further to ring and methyl ($CH_3$) protons (β) to the ring (HSβ + γ). | 1.00-2.00 ppm |
| Aromatic proton | 6.00-10.00 ppm |

HS—Hydrogen Saturated

A sample of Arabian medium crude with a density of 0.8828 Kg/i (15° C./4° C. density using the method described in ASTM D4052) was analyzed by $^1$H NMR spectroscopy. The aliphatic content H (%) types, determined from FIG. 2B, are α=8.48, β=59.59 and γ=26.95. The aromatic H content is 4.97. From this $^1$H NMR spectroscopy, the Brown-Ladner method is used to determine that the oil sample fractional weight composition is 0.2869 naphthenic, 0.5464 paraffinic, and 0.1667 aromatic carbon. The Brown-Ladner method is well-known (as published in Brown and Ladner in Fuel, Vol. 39, January 1960, p. 87-96) to calculate paraffinic, naphthenic and aromatic contents based on the α, β and γ values obtained by $^1$H NMR spectroscopy. The aromatic carbon corresponds to the variable $C_A$ herein, determined at step 330, which in equation (4) herein is expressed as a weight percent, 16.67 W %.

The variable $C_A$, stored at step 335, is applied to step 390. At step 390, Equation (4) and the constants from Table 3B are applied for each of the listed ADs, using the variable $C_A$ stored at step 335, the constants stored at step 305, and the density of the oil sample stored at step 310, as shown below. Each of the determined ADs can be added to the virtual assay of the oil sample. For example, this can be carried out as one step, or as plural steps, for instance, similar to steps 140, 150, 160, 170 and 180 described herein in conjunction with FIG. 1 to calculate a plurality of different elemental composition values/physical properties/indicative properties that make up the virtual assay, for each of a total oil sample, a naphtha fraction, a gas oil fraction, a vacuum gas oil fraction and a vacuum residue fraction, respectively, and to produce the virtual oil sample assay 195 at step 190.

Equation (4) is applied to each of the ADs that make up the virtual assay including those identified in Table 3B, using the corresponding units. In addition, the constants denoted in Table 3B are used as the constants $K_{AD}$, $X1_{AD}$, $X2_{AD}$, $X3_{AD}$, $X4_{AD}$, $X5_AD$, $X6_{AD}$ and $X7_{AD}$) in equation (4); the value $C_A$, determined to be 16.67 W % based on the spectrum in FIG. 2B, is used in equation (4); and the density ρ used in equation (4) of the oil sample under investigation is the 15° C./4° C. density in units of kilograms per liter using the method described in ASTM D4052, which is 0.8828 Kg/L. The calculated AD values are provided for the oil sample under investigation in Table 4B, compared to the actual values obtained using a conventional crude oil assay.

Figure 4:
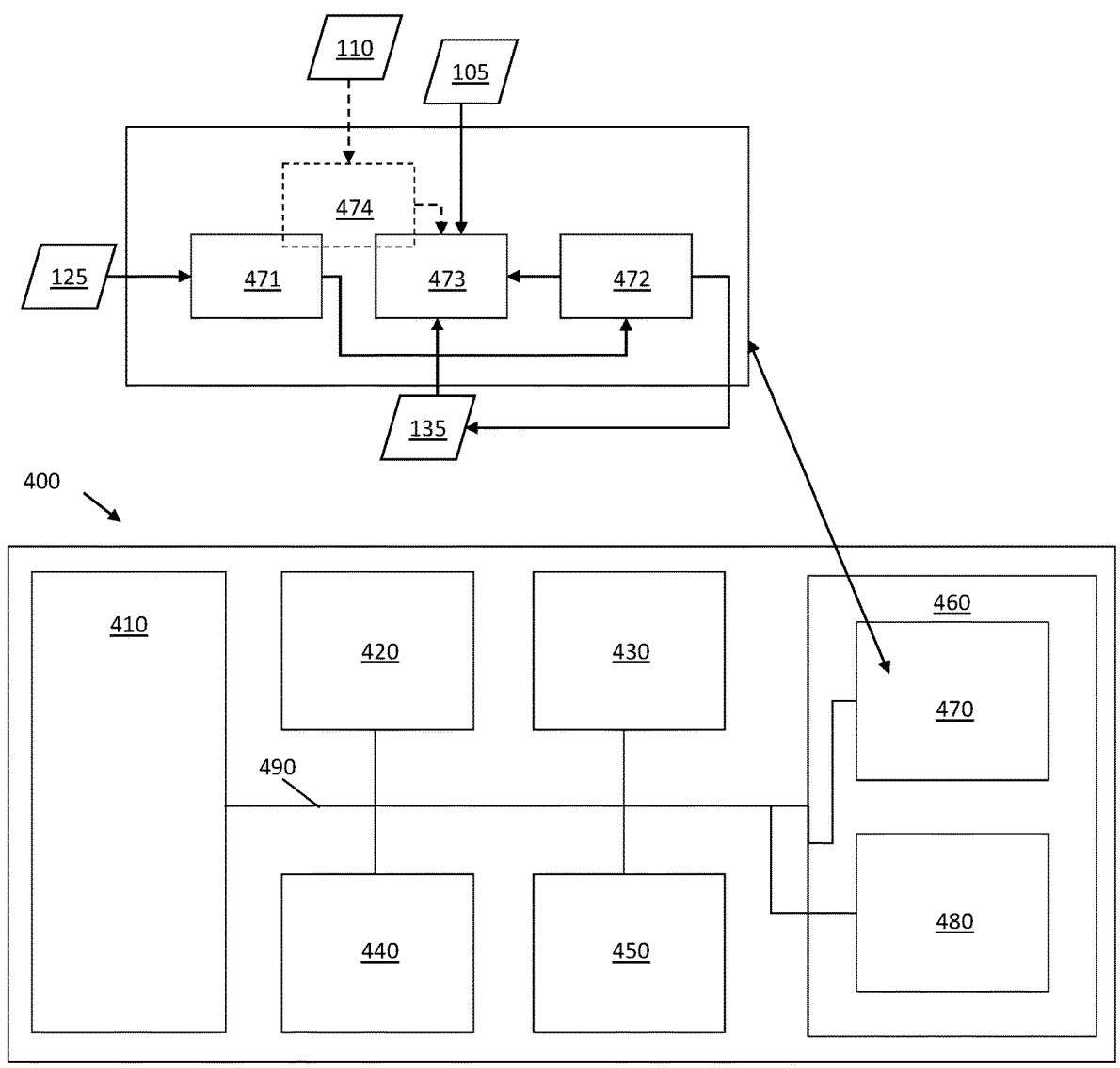
FIG. 4 is a block diagram of a component of a system for implementing the invention, according to one embodiment.

FIG. 4 shows an exemplary block diagram of a computer system 400 in which one embodiment of the present invention can be implemented. Computer system 400 includes a processor 420, such as a central processing unit, an input/output interface 430 and support circuitry 440. In certain embodiments, where the computer system 400 requires a direct human interface, a display 410 and an input device 450 such as a keyboard, mouse, pointer, motion sensor, microphone and/or camera are also provided. The display 410, input device 450, processor 420, and support circuitry 440 are shown connected to a bus 490 which also connects to a memory 460. Memory 460 includes program storage memory 470 and data storage memory 480. Note that while computer system 400 is depicted with direct human interface components display 410 and input device 450, programming of modules and exportation of data can alternatively be accomplished over the input/output interface 430, for instance, where the computer system 400 is connected to a network and the programming and display operations occur on another associated computer, or via a detachable input device as is known with respect to interfacing programmable logic controllers. Program storage memory 470 and data storage memory 480 can each comprise volatile (RAM) and non-volatile (ROM) memory units and can also comprise hard disk and backup storage capacity, and both program storage memory 470 and data storage memory 480 can be embodied in a single memory device or separated in plural memory devices. Program storage memory 470 stores software program modules and associated data and stores one or more of: a raw data receiving module 471, having one or more software programs adapted to receive the analytic characterization data 125, for instance obtained at step 120 in the process flow diagram of FIG. 1; an analytical value calculation module 472, having one or more software programs adapted to determine one or more analytical values or sets of analytical values 135 based on the type of analytic characterization data 125 received by module 471, for instance calculated at step 130 in the process flow diagram of FIG. 1 using the NMR spectra of FIGS. 2A and 2B; one or more assigned assay value calculation modules 473, having one or more software programs adapted to determine a plurality of assigned assay values to produce a virtual assay 195 of an oil sample, for instance using the one or more analytical values 135 calculated by module 472 and the set of constants 105 (and in certain embodiments the density 110), for instance as in step 190 in the process flow diagram of FIG. 1 (in certain embodiments using steps 140, 150, 160, 170 and 180 to calculate and assign a plurality of different elemental composition values/physical properties/indicative properties that make up the virtual assay, for each of a total oil sample, a naphtha fraction, a gas oil fraction, a vacuum gas oil fraction and a vacuum residue fraction, respectively, to produce corresponding assigned assay values for the virtual assay 195, including assigned assay values 145 pertaining to the total oil sample, assigned assay values 155 pertaining to a naphtha fraction, assigned assay values 165 pertaining to a gas oil fraction, assigned assay values 175 pertaining to a vacuum gas oil fraction and assigned assay values 185 pertaining to a vacuum residue fraction); and optionally a density receiving module 474 (in embodiments in which density is used to determine assigned assay values for the virtual assay), shown in dashed lines, having one or more software programs adapted to receive the density data 110, which in certain embodiments can be integrated in the raw data receiving module 471 or the assigned assay value calculation modules 473 (shown by overlapping dashed lines). Data storage memory 480 stores results and other data generated by the one or more program modules of the present invention, including the constants 105, the density 110, the analytic characterization data 125, the one or more analytical values 135, and the assigned assay values (which can be a single set of assigned data values to produce the virtual assay 195, or alternatively delineated by type including the assigned assay values 145, 155, 165, 175 and 185 described herein).

It is to be appreciated that the computer system 400 can be any computer such as a personal computer, minicomputer, workstation, mainframe, a dedicated controller such as a programmable logic controller, or a combination thereof. While the computer system 400 is shown, for illustration purposes, as a single computer unit, the system can comprise a group of computers which can be scaled depending on the processing load and database size.

Computer system 400 generally supports an operating system, for example stored in program storage memory 470 and executed by the processor 420 from volatile memory. According to an embodiment of the invention, the operating system contains instructions for interfacing computer system 400 to the Internet and/or to private networks.

Note that steps 110 and 120 can be carried out separate from or within the computer system 400. For example, step 110 can be carried out and the data entered into the computer system 400, for example via data storage memory 480, or as a single value incorporated in the program storage memory 470 for one or more of the modules. Step 120 can be carried out and the analytic characterization data entered into the computer system 400, for example via data storage memory 480, represented as the analytic characterization data 125.

In alternate embodiments, the present invention can be implemented as a computer program product for use with a computerized computing system. Those skilled in the art will readily appreciate that programs defining the functions of the present invention can be written in any appropriate programming language and delivered to a computer in any form, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the system embodiments can incorporate a variety of computer readable media that comprise a computer usable medium having computer readable code means embodied therein. One skilled in the art will recognize that the software associated with the various processes described can be embodied in a wide variety of computer accessible media from which the software is loaded and activated. Pursuant to In re Beauregard, 35 U.S.P.Q.2d 1383 (U.S. Pat. No. 5,710,578), the present invention contemplates and includes this type of computer readable media within the scope of the invention. In certain embodiments, pursuant to In re Nuijten, 500 F.3d 1346 (Fed. Cir. 2007) (U.S. patent application Ser. No. 09/211,928), the scope of the present claims is limited to computer readable media, wherein the media is both tangible and non-transitory.

It is to be understood that like numerals in the drawings represent like elements through the several figures, and that not all components and/or steps described and illustrated with reference to the figures are required for all embodiments or arrangements. Further, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "including," "comprising," or "having," "containing," "involving," and variations thereof herein, when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Notably, the figures and examples above are not meant to limit the scope of the present disclosure to a single implementation, as other implementations are possible by way of interchange of some or all the described or illustrated elements. Moreover, where certain elements of the present disclosure can be partially or fully implemented using known components, only those portions of such known components that are necessary for an understanding of the present disclosure are described, and detailed descriptions of other portions of such known components are omitted so as not to obscure the disclosure. In the present specification, an implementation showing a singular component should not necessarily be limited to other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present disclosure encompasses present and future known equivalents to the known components referred to herein by way of illustration. The foregoing description of the specific implementations will so fully reveal the general nature of the disclosure that others can, by applying knowledge within the skill of the relevant art(s), readily modify and/or adapt for various applications such specific implementations, without undue experimentation, without departing from the general concept of the present disclosure. Such adaptations and modifications are therefore intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s). It is to be understood that dimensions discussed or shown are drawings are shown accordingly to one example and other dimensions can be used without departing from the disclosure.

The subject matter described above is provided by way of illustration only and should not be construed as limiting. Various modifications and changes can be made to the subject matter described herein without following the example embodiments and applications illustrated and described, and without departing from the true spirit and scope of the invention encompassed by the present disclosure, which is defined by the set of recitations in the following claims and by structures and functions or steps which are equivalent to these recitations.

TABLE 1

| Fraction | Boiling Point, ° C. |
|---|---|
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light gas Oil | 205-260 |
| Mid Gas Oil | 260-315 |
| Heavy gas Oil | 315-370 |
| Light Vacuum Gas Oil | 370-430 |
| Mid Vacuum Gas Oil | 430-480 |
| Heavy vacuum gas oil | 480-565 |
| Vacuum Residue | 565+ |

TABLE 2

| Property | Unit | Property Type | Fraction |
|---|---|---|---|
| Yield | W % or V % | Yield | All |
| API Gravity | ° | Physical | All |
| Kinematic Viscosity @ 38° C. | cSt | Physical | Fraction boiling >250° C. |
| Refractive Index @ 20° C. | Unitless | Physical | Fraction boiling <400° C. |
| Sulfur | W % or ppmw | Composition | All |
| Mercaptan Sulfur | W % | Composition | Fraction boiling <250° C. |
| Nickel | ppmw | Composition | Fraction boiling >400° C. |
| Vanadium | ppmw | Composition | Fraction boiling >400° C. |
| Nitrogen | ppmw | Composition | All |
| Flash Point | ° C. | Indicative | All |
| Cloud Point | ° C. | Indicative | Fraction boiling >250° C. |
| Pour Point | ° C. | Indicative | Fraction boiling >250° C. |
| Freezing Point | ° C. | Indicative | Fraction boiling >250° C. |
| Micro Carbon Residue | W % | Indicative | Fraction boiling >300° C. |
| Smoke Point | mm | Indicative | Fraction boiling between 150-250° C. |
| Octane Number | Unitless | Indicative | Fraction boiling <250° C. |
| Cetane Index | Unitless | Indicative | Fraction boiling between 150-400° C. |
| Aniline Point | ° C. | Indicative | Fraction boiling <520° C. |

TABLE 3A

| ($^{13}$C NMR Constants) | | | | |
|---|---|---|---|---|
| Fraction | property | Units | $K_{AD}$ | $X1_{AD}$ |
| Naphtha | Aromatics (Aro) | W % | 4.383473E+05 | −1.513955E+06 |
| | Hydrogen (H) | W % | 1.160581E+05 | −4.015403E+05 |
| | Paraffins (P) | W % | 5.099900E+06 | −1.764386E+07 |
| | Sulfur (S) | ppmw | −7.321928E+04 | 0.000000E+00 |
| | Octane Number (ON) | Unitless | −1.425731E+06 | 4.928880E+06 |
| Gas Oil (GO) | Aniline Point (AP) | ° C. | −8.558367E+05 | 2.946807E+06 |
| | Cetane Number (CN) | Unitless | −1.571669E+06 | 5.412189E+06 |
| | Cloud Point (CP) | ° C. | −2.082605E+05 | 7.175737E+05 |
| | Nitrogen (N) | Ppmw | −6.743466E+06 | 2.318239E+07 |

TABLE 3A-continued ($^{13}$C NMR Constants)

| Fraction | property | Units | | |
|---|---|---|---|---|
| | Sulfur (S) | Ppmw | −3.816906E+08 | 1.307541E+09 |
| | Kinematic Viscosity @40° C. | cSt | 8.608852E+04 | −2.962618E+06 |
| | Pour Point (PP) | ° C. | −9.503448E+05 | 3.275950E+06 |
| Vacuum Gas Oil (VGO) | Nitrogen (N) | ppmw | 1.683524E+05 | 0.000000E+00 |
| | Sulfur (S) | ppmw | −8.212243E+06 | 0.000000E+00 |
| Vacuum Residue (VR) | Micro Carbon Residue (MCR) | W % | −5.108407E+02 | 0.000000E+00 |
| | Sulfur (S) | ppmw | −1.482555E+07 | 0.000000E+00 |
| Oil Sample | C5-Asphaltenes (C5A) | W % | −3.923691E+04 | 1.346321E+05 |
| | Micro Carbon Resid (MCR) | W % | −4.522094E+05 | 1.555152E+06 |
| | Pour Point (PP) | ° C. | −1.117584E+06 | 3.860835E+06 |
| | Kinematic Viscosity @100° C. | cSt | −4.980508E+05 | 1.719682E+06 |
| | Kinematic Viscosity @70° C. | cSt | −1.395790E+06 | 4.821851E+06 |
| | Nitrogen (N) | ppmw | −2.995704E+07 | 1.025450E+08 |
| | Sulfur (S) | ppmw | −3.222743E+09 | 1.108390E+10 |
| | Total Acid Number (TAN) | mg KOH/100 g | 4.457678E+04 | −1.534633E+05 |
| | Aromatics (Aro) | W % | −5.721262E+05 | 1.967302E+06 |

| Fraction | property | Units | $X2_{AD}$ | $X3_{AD}$ |
|---|---|---|---|---|
| Naphtha | Aromatics (Aro) | W % | 1.743239E+06 | −6.689082E+05 |
| | Hydrogen (H) | W % | 4.621325E+05 | −1.769934E+05 |
| | Paraffins (P) | W % | 2.030860E+07 | −7.781123E+06 |
| | Sulfur (S) | Ppmw | 0.000000E+00 | −1.950211E+05 |
| | Octane Number (ON) | Unitless | −5.666714E+06 | 2.167933E+06 |
| Gas Oil (GO) | Aniline Point (AP) | ° C. | −3.378844E+06 | 1.287670E+06 |
| | Cetane Number (CN) | Unitless | −6.201829E+06 | 2.361664E+06 |
| | Cloud Point (CP) | ° C. | −8.212430E+05 | 3.119740E+05 |
| | Nitrogen (N) | ppmw | −2.652216E+07 | 1.008884E+07 |
| | Sulfur (S) | ppmw | −1.496824E+09 | 5.702632E+08 |
| | Kinematic Viscosity @40° C. | cSt | 3.397190E+05 | −1.294905E+05 |
| | Pour Point (PP) | ° C. | −3.751481E+06 | 1.426742E+06 |
| Vacuum Gas Oil (VGO) | Nitrogen (N) | ppmw | 0.000000E+00 | 6.818106E+04 |
| | Sulfur (S) | ppmw | 0.000000E+00 | −2.971610E+06 |
| Vacuum Residue (VR) | Micro Carbon Resid (MCR) | W % | 0.000000E+00 | 2.004023E+02 |
| | Sulfur (S) | ppmw | 0.000000E+00 | −6.460949E+06 |
| Oil Sample | C5-Asphaltenes (C5A) | W % | −1.546722E+05 | 5.914122E+04 |
| | Micro Carbon Resid (MCR) | W % | −1.783018E+06 | 6.797144E+05 |
| | Pour Point (PP) | ° C. | −4.427401E+06 | 1.685868E+06 |
| | Kinematic Viscosity @100° C. | cSt | −1.981560E+06 | 7.602703E+05 |
| | Kinematic Viscosity @70° C. | cSt | −5.555062E+06 | 2.130707E+06 |
| | Nitrogen (N) | ppmw | −1.173272E+08 | 4.472437E+07 |
| | Sulfur (S) | ppmw | −1.269441E+10 | 4.832808E+09 |
| | Total Acid Number (TAN) | mg KOH/100 g | 1.756245E+05 | −6.676409E+04 |
| | Aromatics (Aro) | W % | −2.250495E+06 | 8.555141E+05 |

| Fraction | property | Units | $X4_{AD}$ | $X5_{AD}$ |
|---|---|---|---|---|
| Naphtha | Aromatics (Aro) | W % | −2.972464E+01 | 1.833654E+00 |
| | Hydrogen (H) | W % | 4.009395E+01 | −5.072789E−01 |
| | Paraffins (P) | W % | 1.503933E+03 | −2.391394E+01 |
| | Sulfur (S) | ppmw | 1.342248E+04 | −2.524415E+03 |
| | Octane Number (ON) | Unitless | −5.034513E+02 | 7.360403E+00 |
| Gas Oil (GO) | Aniline Point (AP) | ° C. | −1.124544E+02 | −1.834457E+01 |
| | Cetane Number (CN) | Unitless | −4.308189E+02 | −2.279396E+01 |
| | Cloud Point (CP) | ° C. | −1.232733E+02 | −1.500016E+00 |
| | Nitrogen (N) | ppmw | −1.582529E+03 | −7.382320E+01 |
| | Sulfur (S) | ppmw | 1.774740E+05 | −1.667278E+04 |
| | Kinematic Viscosity @40° C. | cSt | 4.670084E+00 | 2.171391E+00 |
| | Pour Point (PP) | ° C. | −5.512221E+02 | −2.376291E+00 |
| Vacuum Gas Oil (VGO) | Nitrogen (N) | ppmw | −2.979714E+04 | 2.419057E+03 |
| | Sulfur (S) | ppmw | 1.455933E+06 | −1.172565E+05 |
| Vacuum Residue (VR) | Micro Carbon Resid (MCR) | W % | 1.117165E+02 | −5.444836E+00 |
| | Sulfur (S) | ppmw | 2.627603E+06 | −2.206595E+05 |
| Oil Sample | C5-Asphaltenes (C5A) | W % | 3.135805E+01 | −2.546801E+00 |
| | Micro Carbon Resid (MCR) | W % | 2.162527E+01 | −1.312358E+01 |
| | Pour Point (PP) | ° C. | −7.880369E+02 | 4.613564E+00 |
| | Kinematic Viscosity @100° C. | cSt | 1.068088E+02 | −1.210505E+01 |
| | Kinematic Viscosity @70° C. | cSt | 1.370296E+02 | −2.522038E+01 |
| | Nitrogen (N) | ppmw | 1.652052E+04 | −1.056514E+03 |
| | Sulfur (S) | ppmw | −4.959163E+05 | −6.196289E+04 |
| | Total Acid Number (TAN) | mg KOH/100 g | 2.070862E+01 | 3.016398E−01 |
| | Aromatics (Aro) | W % | −1.748375E+02 | −7.823378E+00 |

| Fraction | property | Units | $X6_{AD}$ | $X7_{AD}$ |
|---|---|---|---|---|
| Naphtha | Aromatics (Aro) | W % | −3.524826E−02 | −2.038192E+00 |
| | Hydrogen (H) | W % | 9.017158E−03 | −3.514183E+01 |
| | Paraffins (P) | W % | 4.366753E−01 | −1.227256E+03 |

TABLE 3A-continued

| | (13C NMR Constants) | | | | |
|---|---|---|---|---|---|
| Gas Oil (GO) | Sulfur (S) | ppmw | | 5.299601E+01 | 2.985637E+04 |
| | Octane Number (ON) | Unitless | | −1.369374E−01 | 4.268691E+02 |
| | Aniline Point (AP) | ° C. | | 3.557543E−01 | 4.840990E+02 |
| | Cetane Number (CN) | Unitless | | 4.381017E−01 | 9.386868E+02 |
| | Cloud Point (CP) | ° C. | | 2.963538E−02 | 1.695027E+02 |
| | Nitrogen (N) | ppmw | | 1.526892E+00 | 3.157442E+03 |
| | Sulfur (S) | ppmw | | 3.249490E+02 | 1.198579E+05 |
| | Kinematic Viscosity @40° C. | cSt | | −4.205263E−02 | −4.744923E+01 |
| | Pour Point (PP) | ° C. | | 3.803047E−02 | 6.835072E+02 |
| Vacuum Gas Oil (VGO) | Nitrogen (N) | ppmw | | −4.881878E+01 | −1.113681E+04 |
| | Sulfur (S) | ppmw | | 2.376839E+03 | 5.152892E+05 |
| Vacuum Residue (VR) | Micro Carbon Resid (MCR) | W % | | 1.169339E−01 | −3.422130E+01 |
| | Sulfur (S) | ppmw | | 4.477281E+03 | 1.093089E+06 |
| Oil Sample | C5-Asphaltenes (C5A) | W % | | 5.001134E−02 | 1.300803E+01 |
| | Micro Carbon Resid (MCR) | W % | | 2.568410E−01 | 2.277559E+02 |
| | Pour Point (PP) | ° C. | | −1.030613E−01 | 8.225115E+02 |
| | Kinematic Viscosity @100° C. | cSt | | 2.347595E−01 | 1.129028E+02 |
| | Kinematic Viscosity @70° C. | cSt | | 4.907170E−01 | 3.311247E+02 |
| | Nitrogen (N) | ppmw | | 2.079086E+01 | 1.372267E+03 |
| | Sulfur (S) | ppmw | | 1.196844E+03 | 1.772612E+06 |
| | Total Acid Number (TAN) | mg KOH/100 g | | −5.458524E−03 | −2.987423E+01 |
| | Aromatics (Aro) | W % | | 1.602398E−01 | 3.432393E+02 |

TABLE 3B

| | (1H NMR Constants) | | | |
|---|---|---|---|---|
| Fraction | property | Units | $K_{AD}$ | $X1_{AD}$ |
| Naphtha | Aromatics (Aro) | W % | 1.163326E+06 | −4.058109E+06 |
| | Hydrogen (H) | W % | −2.994033E+05 | 1.040358E+06 |
| | Paraffins (P) | W % | −1.251204E+07 | 4.363847E+07 |
| | Sulfur (S) | ppmw | −2.266078E+06 | 0.000000E+00 |
| | Octane Number (ON) | Unitless | 3.222716E+06 | −1.124218E+07 |
| Gas Oil (GO) | Aniline Point (AP) | ° C. | 1.250720E+05 | −4.586701E+05 |
| | Cetane Number (CN) | Unitless | 1.882123E+05 | −6.634751E+05 |
| | Cloud Point (CP) | ° C. | −1.835473E+05 | 7.234794E+05 |
| | Nitrogen (N) | ppmw | −1.363808E+06 | 6.103463E+06 |
| | Sulfur (S) | ppmw | 2.467374E+08 | −9.290318E+08 |
| | Kinematic Viscosity @40° C. | cSt | −2.391398E+04 | 9.120858E+04 |
| | Pour Point (PP) | ° C. | −1.988544E+04 | 5.817089E+04 |
| Vacuum Gas Oil (VGO) | Nitrogen (N) | ppmw | 2.192772E+06 | 0.000000E+00 |
| | Sulfur (S) | ppmw | −1.165167E+08 | 0.000000E+00 |
| Vacuum Residue (VR) | Micro Carbon Residue (MCR) | W % | −1.701664E+04 | 0.000000E+00 |
| | Sulfur (S) | ppmw | −2.217164E+08 | 0.000000E+00 |
| Oil Sample | C5-Asphaltenes (C5A) | W % | −2.494203E+03 | 1.867019E+04 |
| | Micro Carbon Resid (MCR) | W % | −1.744558E+04 | 1.026002E+05 |
| | Pour Point (PP) | ° C. | −1.427440E+06 | 5.265152E+06 |
| | Kinematic Viscosity @100° C. | cSt | −1.701958E+05 | 5.995657E+05 |
| | Kinematic Viscosity @70° C. | cSt | −6.520504E+05 | 2.295680E+06 |
| | Nitrogen (N) | ppmw | −4.700356E+07 | 1.770995E+08 |
| | Sulfur (S) | ppmw | 6.903462E+08 | −2.628437E+09 |
| | Total Acid Number (TAN) | mg KOH/100 g | −4.384825E+02 | 3.440653E+03 |
| | Aromatics (Aro) | W % | −4.404178E+05 | 1.702112E+06 |
| Fraction | property | Units | $X2_{AD}$ | $X3_{AD}$ |
| Naphtha | Aromatics (Aro) | W % | 4.666524E+06 | −1.784121E+06 |
| | Hydrogen (H) | W % | −1.196856E+06 | 4.575169E+05 |
| | Paraffins (P) | W % | −5.015232E+07 | 1.915255E+07 |
| | Sulfur (S) | ppmw | 0.000000E+00 | 1.034842E+06 |
| | Octane Number (ON) | Unitless | 1.291482E+07 | −4.936654E+06 |
| Gas Oil (GO) | Aniline Point (AP) | ° C. | 5.168471E+05 | −1.934881E+05 |
| | Cetane Number (CN) | Unitless | 7.481995E+05 | −2.806777E+05 |

TABLE 3B-continued

| | | | ($^3$H NMR Constants) | |
|---|---|---|---|---|
| | Cloud Point (CP) | ° C. | −8.119692E+05 | 3.040765E+05 |
| | Nitrogen (N) | ppmw | −6.723171E+06 | 2.365396E+06 |
| | Sulfur (S) | ppmw | 1.049766E+09 | 3.954521E+08 |
| | Kinematic Viscosity @40° C. | cSt | −1.026546E+05 | 3.832798E+04 |
| | Pour Point (PP) | ° C. | −7.138175E+04 | 3.362130E+04 |
| Vacuum Gas Oil (VGO) | Nitrogen (N) | ppmw | 0.000000E+00 | −2.816074E+06 |
| | Sulfur (S) | ppmw | 0.000000E+00 | 1.221790E+08 |
| Vacuum Residue (VR) | Micro Carbon Resid (MCR) | W % | 0.000000E+00 | −6.504249E+03 |
| | Sulfur (S) | ppmw | 0.000000E+00 | 2.207459E+08 |
| Oil Sample | C5-Asphaltenes (C5A) | W % | −2.032909E+04 | 7.181490E+03 |
| | Micro Carbon Resid (MCR) | W % | −1.123896E+05 | 4.008372E+04 |
| | Pour Point (PP) | ° C. | −5.980621E+06 | 2.282122E+06 |
| | Kinematic Viscosity @100° C. | cSt | −7.010785E+05 | 2.738228E+05 |
| | Kinematic Viscosity @70° C. | cSt | −2.659812E+06 | 1.027965E+06 |
| | Nitrogen (N) | ppmw | −2.003972E+08 | 7.556116E+07 |
| | Sulfur (S) | ppmw | 2.965960E+09 | −1.113030E+09 |
| | Total Acid Number (TAN) | mg KOH/100 g | 3.567070E+03 | 9.656335E+02 |
| | Aromatics (Aro) | W % | −1.902740E+06 | 7.050713E+05 |

| Fraction | property | Units | X4$_{AD}$ | X5$_{AD}$ |
|---|---|---|---|---|
| Naphtha | Aromatics (Aro) | W % | 2.608251E+03 | −1.356925E+02 |
| | Hydrogen (H) | W % | −4.082172E+02 | 1.520738E+01 |
| | Paraffins (P) | W % | −2.895214E+04 | 1.408330E+03 |
| | Sulfur (S) | ppmw | 4.836396E+05 | −2.409214E+04 |
| | Octane Number (ON) | Unitless | 7.715215E+03 | −4.310522E+02 |
| Gas Oil (GO) | Aniline Point (AP) | ° C. | 2.123427E+03 | −1.350716E+02 |
| | Cetane Number (CN) | Unitless | 1.544768E+03 | −9.610425E+01 |
| | Cloud Point (CP) | ° C. | −6.177373E+03 | 4.088776E+02 |
| | Nitrogen (N) | ppmw | −9.806325E+04 | 5.674525E+03 |
| | Sulfur (S) | ppmw | 5.375383E+06 | −3.533174E+05 |
| | Kinematic Viscosity @40° C. | cSt | −6.161637E+02 | 3.920660E+01 |
| | Pour Point (PP) | ° C. | 9.506873E+02 | −2.604452E+01 |
| Vacuum Gas Oil (VGO) | Nitrogen (N) | ppmw | −5.123373E+05 | 1.197606E+04 |
| | Sulfur (S) | ppmw | 2.651072E+07 | −8.036516E+05 |
| Vacuum Residue (VR) | Micro Carbon Resid (MCR) | W % | 3.268210E+03 | −2.661028E+02 |
| | Sulfur (S) | ppmw | 5.019316E+07 | −1.608002E+06 |
| Oil Sample | C5-Asphaltenes (C5A) | W % | −6.463805E+02 | 4.106220E+01 |
| | Micro Carbon Resid (MCR) | W % | −2.762549E+03 | 1.742477E+02 |
| | Pour Point (PP) | ° C. | −2.276137E+04 | 1.636370E+03 |
| | Kinematic Viscosity @100° C. | cSt | −1.500529E+02 | 1.608732E+01 |
| | Kinematic Viscosity @70° C. | cSt | −1.675382E+03 | 1.174908E+02 |
| | Nitrogen (N) | ppmw | −1.024873E+06 | 6.741529E+04 |
| | Sulfur (S) | ppmw | 1.704711E+07 | −1.102014E+06 |
| | Total Acid Number (TAN) | mg KOH/100 g | −1.371396E+02 | 6.954937E+00 |
| | Aromatics (Aro) | W % | −1.327669E+04 | 8.391171E+02 |

| Fraction | property | Units | X6$_{AD}$ | X7$_{AD}$ |
|---|---|---|---|---|
| Naphtha | Aromatics (Aro) | W % | 3.042355E+00 | −6.795217E+02 |
| | Hydrogen (H) | W % | −3.505713E−01 | 2.157202E+02 |
| | Paraffins (P) | W % | −3.142702E+01 | 9.072928E+03 |
| | Sulfur (S) | ppmw | 5.676464E+02 | −1.659332E+05 |
| | Octane Number (ON) | Unitless | 9.390150E+00 | −1.289485E+03 |
| Gas Oil (GO) | Aniline Point (AP) | ° C. | 2.976595E+00 | −9.660136E+01 |
| | Cetane Number (CN) | Unitless | 2.085601E+00 | −7.722152E+01 |
| | Cloud Point (CP) | ° C. | −8.926625E+00 | −5.786703E+01 |
| | Nitrogen (N) | ppmw | −1.273849E+02 | 1.602908E+04 |
| | Sulfur (S) | ppmw | 7.704385E+03 | 1.769561E+04 |

TABLE 3B-continued (¹H NMR Constants)

| | | | | |
|---|---|---|---|---|
| | Kinematic Viscosity @40° C. | cSt | −8.636547E−01 | 2.772162E+01 |
| | Pour Point (PP) | ° C. | 7.084948E−01 | −7.386625E+02 |
| Vacuum Gas Oil (VGO) | Nitrogen (N) | ppmw | −3.516192E+02 | 4.475853E+05 |
| | Sulfur (S) | ppmw | 2.152101E+04 | −1.942172E+07 |
| Vacuum Residue (VR) | Micro Carbon Resid (MCR) | W % | 5.676002E+00 | 9.972868E+02 |
| | Sulfur (S) | ppmw | 4.240295E+04 | −3.509076E+07 |
| Oil Sample | C5-Asphaltenes (C5A) | W % | −9.083984E−01 | 3.318774E+01 |
| | Micro Carbon Resid (MCR) | W % | −3.850013E+00 | 1.598952E+02 |
| | Pour Point (PP) | ° C. | −3.525129E+01 | −2.842558E+03 |
| | Kinematic Viscosity @100° C. | cSt | −3.707756E−01 | −9.203164E+01 |
| | Kinematic Viscosity @70° C. | cSt | −2.588987E+00 | −1.109447E+02 |
| | Nitrogen (N) | ppmw | −1.479580E+03 | 3.839702E+03 |
| | Sulfur (S) | ppmw | 2.416402E+04 | −3.753731E+05 |
| | Total Acid Number (TAN) | mg KOH/100 g | −1.593124E−01 | 4.132879E+01 |
| | Aromatics (Aro) | W % | −1.836981E+01 | 6.004811E+02 |

TABLE 4A (¹³C NMR Calculations)

| AD Description | Unit | Conventional Crude Oil Assay Value | Calculated AD Value (Equation (4)) |
|---|---|---|---|
| Naphtha, Aro | W % | 11.0 | 10.6 |
| Naphtha, H | W % | 14.7 | 14.6 |
| Naphtha, P | W % | 75.8 | 70.8 |
| Naphtha, S | ppmw | 876 | 876 |
| Naphtha, ON | Unitless | 52.5 | 56.6 |
| GO, AP | ° C. | 66.0 | 66.1 |
| GO, CN | Unitless | 59.5 | 59.6 |
| GO, CP | ° C. | −10.0 | −10.1 |
| GO, N | ppmw | 71.2 | 107.5 |
| GO, S | ppmw | 13,090 | 10,415 |
| GO, Kinematic Viscosity @40° C. | cSt | 2.9 | 2.9 |
| GO, PP | ° C. | −9.0 | −9.1 |
| VGO, N | ppmw | 617 | 617 |
| VGO, S | ppmw | 28,800 | 28,800 |
| VR, MCR | W % | 12.4 | 12.4 |
| VR, S | ppmw | 52,700 | 52,700 |
| Oil Sample, C5A | W % | 1.4 | 1.4 |
| Oil Sample, MCR | W % | 6.2 | 6.3 |
| Oil Sample, PP | ° C. | −15.0 | −16.0 |
| Oil Sample, Kinematic Viscosity @100° C. | cSt | 11.8 | 11.8 |
| Oil Sample, Kinematic Viscosity @70° C. | cSt | 21.7 | 21.8 |
| Oil Sample, N | ppmw | 829 | 813 |
| Oil Sample, S | ppmw | 30,000 | 30,580 |
| Oil Sample, TAN | mg KOH/100 g | 0.1 | 0.1 |
| Oil Sample, Aro | W % | 20.2 | 19.4 |

TABLE 4B (¹H NMR Calculations)

| AD Description | Unit | Conventional Crude Oil Assay Value | Calculated AD Value (Equation (4)) |
|---|---|---|---|
| Naphtha, Aro | W % | 11.0 | 11.0 |
| Naphtha, H | W % | 14.7 | 14.7 |
| Naphtha, P | W % | 75.8 | 75.7 |
| Naphtha, S | ppmw | 876 | 876 |
| Naphtha, ON | Unitless | 52.5 | 52.5 |
| GO, AP | ° C. | 66.0 | 65.9 |
| GO, CN | Unitless | 59.5 | 59.5 |
| GO, CP | ° C. | −10.0 | −10.0 |
| GO, N | ppmw | 71.2 | 71.3 |
| GO, S | ppmw | 13,090 | 13,051 |
| GO, Kinematic Viscosity @40° C. | cSt | 2.9 | 2.9 |
| GO, PP | ° C. | −9.0 | −9.0 |
| VGO, N | ppmw | 617 | 617 |
| VGO, S | ppmw | 28,800 | 28,800 |
| VR, MCR | W % | 12.4 | 12.4 |
| VR, S | ppmw | 52,700 | 52,700 |
| Oil Sample, C5A | W % | 1.4 | 1.4 |
| Oil Sample, MCR | W % | 6.2 | 6.2 |
| Oil Sample, PP | ° C. | −15.0 | −15.0 |
| Oil Sample, Kinematic Viscosity @100° C. | cSt | 11.8 | 11.8 |
| Oil Sample, Kinematic Viscosity @70° C. | cSt | 21.7 | 21.7 |
| Oil Sample, N | ppmw | 829 | 828 |
| Oil Sample, S | ppmw | 30,000 | 29,893 |
| Oil Sample, TAN | mg KOH/100 g | 0.1 | 0.1 |
| Oil Sample, Aro | W % | 20.2 | 20.2 |

The invention claimed is:

1. A method for producing a virtual assay of an oil sample, wherein the oil sample is characterized by a density, wherein the oil sample is selected from a group consisting of crude oil, bitumen and shale oil, and wherein the oil sample is characterized by a naphtha fraction, a gas oil fraction, a vacuum gas oil fraction and a vacuum residue fraction, the method comprising:

preparing a solution of the oil sample by mixing the oil sample with a nuclear magnetic resonance (NMR) spectroscopy solvent;

operating an NMR spectrometer with the solution to obtain NMR spectroscopy data by directly analyzing the oil sample without distillation;

entering into a computer, the NMR spectroscopy data, wherein the NMR spectroscopy data is indicative of aromatic content, and optionally one or both of paraffinic content and naphthenic content, of the oil sample, wherein the aromatic content, and the optionally one or both of the paraffinic content and the naphthenic content, are used as one or more analytical values (AVs); and calculating and assigning, as a function of the one or more AVs, and the density of the oil sample, virtual assay data of the oil sample and the naphtha fraction, the gas oil fraction, the vacuum gas oil fraction and the vacuum residue fractions, the virtual assay data comprising a plurality of assigned assay data values, wherein the virtual assay data is used to evaluate the oil sample without distillation and is used to determine an appropriate refinery or refining unit, wherein the virtual assay data comprises:
the plurality of assigned assay data values pertaining to the oil sample including one or more of the aromatic content, C5-asphaltenes content, elemental composition of sulfur and elemental composition of nitrogen, micro-carbon residue content, total acid number and viscosity;
the plurality of assigned assay data values pertaining to the vacuum residue fraction of the oil sample including one or more of the elemental composition of sulfur and the micro-carbon residue content;
the plurality of assigned assay data values pertaining to the vacuum gas oil fraction of the oil sample including one or more of the elemental composition of sulfur and the elemental composition of nitrogen;
the plurality of assigned assay data values pertaining to the gas oil fraction of the oil sample including one or more of the elemental composition of sulfur and the elemental composition of nitrogen, the viscosity, and indicative properties including aniline point, cetane number, cloud point and pour point; and
the plurality of assigned assay data values pertaining to the naphtha fraction of the oil sample including one or more of the aromatic content, elemental composition of hydrogen and the elemental composition of sulfur, paraffin content and octane number.

2. The method of claim 1, wherein the virtual assay data comprises:
the plurality of assigned assay data values pertaining to the oil sample including the aromatic content, the C5-asphaltenes content, the elemental composition of sulfur and the elemental composition of nitrogen, the micro-carbon residue content, the total acid number and the viscosity;
the plurality of assigned assay data values pertaining to the vacuum residue fraction of the oil sample including the elemental composition of sulfur and the micro-carbon residue content;
the plurality of assigned assay data values pertaining to the vacuum gas oil fraction of the oil sample including the elemental composition of sulfur and the elemental composition of nitrogen;
the plurality of assigned assay data values pertaining to the gas oil fraction of the oil sample including the elemental composition of sulfur and the elemental composition of nitrogen, the viscosity, and the indicative properties including the aniline point, the cetane number, the cloud point and the pour point; and
the plurality of assigned assay data values pertaining to the naphtha fraction of the oil sample including the aromatic content, the elemental composition of hydrogen and the elemental composition of sulfur, the paraffin content and the octane number.

3. The method of claim 2, wherein the virtual assay data further comprises:
yields of fractions from the oil sample as mass fractions of boiling point ranges, including one or more of naphtha, gas oil, vacuum gas oil and vacuum residue;
composition information of hydrogen sulfide and/or mercaptans in the oil sample and/or corresponding fractions;
elemental compositions of one or more of carbon, hydrogen, nickel, and vanadium;
physical properties of the oil sample and/or corresponding fractions including one or more of API gravity and refractive index; or
indicative properties of the oil sample and/or corresponding fractions including one or more of flash point, freezing point and smoke point.

4. The method of claim 1, wherein the nuclear magnetic resonance spectrometer employs $^1$H active nuclei to derive the aromatic content, and the optionally one or both of the paraffinic content and the naphthenic content.

5. The method of claim 1, wherein the nuclear magnetic resonance spectrometer employs $^{13}$C active nuclei to derive the aromatic content, and the optionally one or both of the paraffinic content and the naphthenic content.

6. The method of claim 1, wherein each assigned assay data value is calculated and assigned by a multi-variable polynomial equation with predetermined constant coefficients developed using linear regression techniques, wherein corresponding variables are the one or more AVs, and the density of the oil sample.

7. The method of claim 6, wherein each assigned assay data value is calculated and assigned by $$AD = K_{AD} + X1_{AD}*AV + X2_{AD}*AV^2 + X3_{AD}*AV^3 + X4_{AD}*\rho*AV$$

where:
AD is the assigned assay data value that is a value and/or property representative of an elemental composition value, a physical property or an indicative property;
AV is a single analytical value of the oil sample;
$\rho$ is the density of the oil sample; and
$K_{AD}$, $X1_{AD}$, $X2_{AD}$, $X3_{AD}$, and $X4_{AD}$ are constants.

8. The method of claim 6, wherein each assigned assay data value is calculated and assigned by $$AD = K_{AD} + X1_{AD}*\rho + X2_{AD}*\rho^2 + X3_{AD}*\rho^3 + X4_{AD}*AV + X5_{AD}*AV^2 + X6_{AD}*AV^3 + X7_{AD}*\rho*AV$$

where:
AD is the assigned assay data value that is a value and/or property representative of an elemental composition value, a physical property or an indicative property;
AV is a single analytical value of the oil sample;
$\rho$ is the density of the oil sample; and
$K_{AD}$, $X1_{AD}$, $X2_{AD}$, $X3_{AD}$, $X4_{AD}$, $X5_{AD}$, $X6_{AD}$ and $X7_{AD}$ are constants.

9. The method of claim 1, wherein the one or more AVs is the aromatic content of the oil sample as determined by the NMR spectroscopy data.

10. A system for producing a virtual assay of an oil sample, wherein the oil sample is characterized by a density, wherein the oil sample is selected from a group consisting of crude oil, bitumen and shale oil, and wherein the oil sample is characterized by a naphtha fraction, a gas oil fraction, a vacuum gas oil fraction and a vacuum residue fraction, the system comprising:

a nuclear magnetic resonance (NMR) spectrometer that outputs NMR spectroscopy data;

a non-volatile memory device that stores calculation modules and data, the data including the NMR spectroscopy data, wherein the NMR spectroscopy data is indicative of aromatic content, and optionally one or both of paraffinic content and naphthenic content, of the oil sample, obtained by NMR spectroscopy of a solution of the oil sample without distillation in an NMR spectroscopy solvent, wherein the aromatic content, and the optionally one or both of the paraffinic content and the naphthenic content, are used as one or more analytical values (AVs);

a processor coupled to the non-volatile memory device; and a calculation module that is stored in the non-volatile memory device and that is executed by the processor, wherein the calculation module calculates, as a function of the one or more AVs and the density of the oil sample, virtual assay data of the oil sample and the naphtha fraction, the gas oil fraction, the vacuum gas oil fraction and the vacuum residue fraction, the virtual assay data comprising a plurality of assigned assay data values, wherein the virtual assay data is used to evaluate the oil sample without distillation and is used to determine an appropriate refinery or refining unit, wherein the virtual assay data comprises:
the plurality of assigned assay data values pertaining to the oil sample including one or more of the aromatic content, C5-asphaltenes content, elemental composition of sulfur and elemental composition of nitrogen, micro-carbon residue content, total acid number and viscosity;
the plurality of assigned assay data values pertaining to the vacuum residue fraction of the oil sample including one or more of the elemental composition of sulfur and the micro-carbon residue content;
the plurality of assigned assay data values pertaining to the vacuum gas oil fraction of the oil sample including one or more of the elemental composition of sulfur and the elemental composition of nitrogen;
the plurality of assigned assay data values pertaining to the gas oil fraction of the oil sample including one or more of the elemental composition of sulfur and the elemental composition of nitrogen, the viscosity, and indicative properties including aniline point, cetane number, cloud point and pour point; and
the plurality of assigned assay data values pertaining to the naphtha fraction of the oil sample including one or more of the aromatic content, elemental composition of hydrogen and the elemental composition of sulfur, paraffin content and octane number.

11. The system as in claim 10, wherein the virtual assay data comprises:
the plurality of assigned assay data values pertaining to the oil sample including the aromatic content, the C5-asphaltenes content, the elemental composition of sulfur and the elemental composition of nitrogen, the micro-carbon residue content, the total acid number and the viscosity;
the plurality of assigned assay data values pertaining to the vacuum residue fraction of the oil sample including the elemental composition of sulfur and the micro-carbon residue content;
the plurality of assigned assay data values pertaining to the vacuum gas oil fraction of the oil sample including the elemental composition of sulfur and the elemental composition of nitrogen;
the plurality of assigned assay data values pertaining to the gas oil fraction of the oil sample including the elemental composition of sulfur and the elemental composition nitrogen, the viscosity, and the indicative properties including the aniline point, the cetane number, the cloud point and the pour point; and
the plurality of assigned assay data values pertaining to the naphtha fraction of the oil sample including the aromatic content, the elemental composition of hydrogen and the elemental composition of sulfur, the paraffin content and the octane number.

12. The system as in claim 11, wherein the virtual assay data further comprises:
yields of fractions from the oil sample as mass fractions of boiling point ranges, including one or more of naphtha, gas oil, vacuum gas oil and vacuum residue;
composition information of hydrogen sulfide and/or mercaptans in the oil sample and/or the corresponding fractions;
elemental compositions of one or more of carbon, hydrogen, nickel, and vanadium;
physical properties of the oil sample and/or the corresponding fractions including one or more of API gravity and refractive index; or
indicative properties of the oil sample and/or the corresponding fractions including one or more of flash point, freezing point and smoke point.

13. The system of claim 10, wherein the nuclear magnetic resonance spectrometer employs $^1H$ active nuclei to derive the aromatic content, and the optionally one or both of the paraffinic content and the naphthenic content.

14. The system of claim 10, wherein the nuclear magnetic resonance spectrometer employs $^{13}C$ active nuclei to derive the aromatic content, and the optionally one or both of the paraffinic content and the naphthenic content.

15. The system of claim 10, wherein each assigned assay data value is calculated by the calculation module with a multi-variable polynomial equation with predetermined constant coefficients developed using linear regression techniques, wherein corresponding variables are the aromatic content, and the optionally one or both of the paraffinic content and the naphthenic content, and the density of the oil sample.

16. The system of claim 15, wherein each assigned assay data value is calculated by the calculation module with a function:

$$AD = K_{AD} + X1_{AD}*AV + X2_{AD}*AV^2 + X3_{AD}*AV^3 + X4_{AD}*\rho*AV$$

where:
AD is the assigned assay data value that is a value and/or property representative of an elemental composition value, a physical property or an indicative property;
AV is a single analytical value of the oil sample;
$\rho$ is the density of the oil sample; and
$K_{AD}$, $X1_{AD}$, $X2_{AD}$, $X3_{AD}$, and $X4_{AD}$ are constants.

17. The system of claim 15, wherein each assigned assay data value is calculated by the calculation module with a function:

$$AD = K_{AD} + X1_{AD}*\rho + X2_{AD}*\rho^2 + X3_{AD}*\rho^3 + X4_{AD}*AV + X5_{AD}*AV^2 + X6_{AD}*AV^3 + X7_{AD}*\rho*AV$$

where:
AD is the assigned assay data value that is a value and/or property representative of an elemental composition value, a physical property or an indicative property;
AV is a single analytical value of the oil sample;
$\rho$ is the density of the oil sample; and
$K_{AD}$, $X1_{AD}$, $X2_{AD}$, $X3_{AD}$, $X4_{AD}$, $X5_{AD}$, $X6_{AD}$ and $X7_{AD}$ are constants.

18. The system of claim 17, wherein the one or more AVs is the aromatic content of the oil sample as obtained by the NMR spectroscopy.

\* \* \* \* \*